US010816553B2

(12) United States Patent
Rajasekaran et al.

(10) Patent No.: US 10,816,553 B2
(45) Date of Patent: Oct. 27, 2020

(54) METHODS AND COMPOSITIONS FOR AMPLIFIED ELECTROCHEMILUMINESCENCE DETECTION

(71) Applicant: VIBRANT HOLDINGS, LLC, Hillsborough, CA (US)

(72) Inventors: John J. Rajasekaran, Hillsborough, CA (US); Vasanth Jayaraman, San Mateo, CA (US); Tianhao Wang, San Mateo, CA (US); Kang Bei, San Mateo, CA (US); Hari Krishnan Krishnamurthy, San Mateo, CA (US)

(73) Assignee: Vibrant Holdings, LLC, San Carlos, CA (US)

( * ) Notice: Subject to any disclaimer, the term of this patent is extended or adjusted under 35 U.S.C. 154(b) by 297 days.

(21) Appl. No.: 14/768,196

(22) PCT Filed: Feb. 17, 2014

(86) PCT No.: PCT/US2014/016737
§ 371 (c)(1),
(2) Date: Aug. 14, 2015

(87) PCT Pub. No.: WO2014/127328
PCT Pub. Date: Aug. 21, 2014

(65) Prior Publication Data

US 2017/0192007 A1 Jul. 6, 2017

Related U.S. Application Data

(60) Provisional application No. 61/765,584, filed on Feb. 15, 2013.

(51) Int. Cl.
*G01N 33/533* (2006.01)
*G01N 33/58* (2006.01)
(Continued)

(52) U.S. Cl.
CPC .......... *G01N 33/582* (2013.01); *G01N 21/66* (2013.01); *G01N 33/5438* (2013.01); *G01N 33/54373* (2013.01); *G01N 33/581* (2013.01)

(58) Field of Classification Search
CPC ..... G01N 33/582; G01N 21/66; G01N 33/581
See application file for complete search history.

(56) References Cited

U.S. PATENT DOCUMENTS 5,143,854 A 9/1992 Pirrung et al.
5,240,811 A 8/1993 Taylor et al.
(Continued)

FOREIGN PATENT DOCUMENTS

JP H05-294995 A 11/1993
JP H06-500308 A 1/1994
(Continued)

OTHER PUBLICATIONS

Gschneidner, "Physical Properties of the Rare Earth Metal", Bulletin of Alloy Phase Diagrams, vol. 11, No. 3, 1990, pp. 216-224. (Year: 1990).*
(Continued)

*Primary Examiner* — Christopher L Chin
(74) *Attorney, Agent, or Firm* — Goodwin Proctor LLP

(57) ABSTRACT

Disclosed herein are formulations, substrates, and arrays. Also disclosed herein are methods for manufacturing and using the formulations, substrates, and arrays. Also disclosed are methods for identifying peptide sequences useful for diagnosis and treatment of disorders, and methods for using the peptide sequences for diagnosis and treatment of disorders, e.g., celiac disorder. In certain embodiments, substrates and arrays comprise a porous layer for synthesis and attachment of polymers or biomolecules.

20 Claims, 14 Drawing Sheets

Tyramide Signal Amplification Assay

HRP
$H_2O_2$
Tyr + Flu Tag
HRP

Assay capture Ab+protein
Sec Ab with HRP

Amplification by HRP

(51) Int. Cl.
*G01N 33/543* (2006.01)
*G01N 21/66* (2006.01)

(56) References Cited

U.S. PATENT DOCUMENTS

| | | | | |
|---|---|---|---|---|
| 5,310,687 | A | 5/1994 | Bard et al. | |
| 5,866,434 | A * | 2/1999 | Massey | B82Y 30/00 435/176 |
| 5,919,523 | A | 7/1999 | Sundberg et al. | |
| 6,017,696 | A | 1/2000 | Heller | |
| 6,040,138 | A | 3/2000 | Lockhart et al. | |
| 6,083,697 | A | 7/2000 | Beecher et al. | |
| 6,140,045 | A * | 10/2000 | Wohlstadter | G01N 21/66 204/400 |
| 6,319,726 | B1 | 11/2001 | Schuppan et al. | |
| 6,506,558 | B1 | 1/2003 | Fodor et al. | |
| 6,521,181 | B1 | 2/2003 | Northrup et al. | |
| 6,943,034 | B1 | 9/2005 | Winkler et al. | |
| 7,510,841 | B2 | 3/2009 | Stuelpnagel et al. | |
| 7,544,638 | B2 | 6/2009 | Gao et al. | |
| 8,128,908 | B2 * | 3/2012 | Santra | A61K 49/0002 424/9.3 |
| 8,221,597 | B2 | 7/2012 | Lee et al. | |
| 9,417,236 | B2 | 8/2016 | Rajasekaran et al. | |
| 2003/0068446 | A1 | 4/2003 | Mirkin et al. | |
| 2003/0124029 | A1 | 7/2003 | Webb et al. | |
| 2003/0148401 | A1 | 8/2003 | Agrawal et al. | |
| 2003/0228605 | A1 | 12/2003 | Sloostra et al. | |
| 2005/0221351 | A1 | 10/2005 | Ryu | |
| 2005/0244863 | A1 | 11/2005 | Mir | |
| 2005/0260611 | A1 | 11/2005 | Wang et al. | |
| 2006/0088863 | A1 | 4/2006 | Yamamoto et al. | |
| 2006/0172340 | A1 | 8/2006 | Wohlstadter et al. | |
| 2007/0122841 | A1 | 5/2007 | Rajasekaran et al. | |
| 2007/0122842 | A1 | 5/2007 | Rajasekaran et al. | |
| 2007/0154946 | A1 | 7/2007 | Rajasekaran et al. | |
| 2007/0231794 | A1 | 10/2007 | Dill et al. | |
| 2008/0108149 | A1 | 5/2008 | Sundararajan et al. | |
| 2009/0311727 | A1 | 12/2009 | Watkins et al. | |
| 2009/0325816 | A1 | 12/2009 | Mirkin et al. | |
| 2010/0028559 | A1 | 2/2010 | Yan et al. | |
| 2010/0093554 | A1 | 4/2010 | Chu | |
| 2010/0120630 | A1 | 5/2010 | Huang et al. | |
| 2010/0240555 | A1 | 9/2010 | Sundararajan et al. | |
| 2011/0097762 | A1 | 4/2011 | Gao et al. | |
| 2011/0281766 | A1 | 11/2011 | Cooper | |
| 2012/0172309 | A1 | 7/2012 | Dal Farra et al. | |
| 2012/0183981 | A1 | 7/2012 | Norman et al. | |
| 2012/0190590 | A1 | 7/2012 | Wohlstadter et al. | |
| 2012/0245057 | A1 | 9/2012 | Albert et al. | |
| 2014/0072963 | A1 * | 3/2014 | Qin | G01N 33/582 435/5 |
| 2017/0168047 | A1 * | 6/2017 | Aghvanyan | G01N 33/54393 |

FOREIGN PATENT DOCUMENTS

| | | | |
|---|---|---|---|
| JP | 2002-500362 | A | 1/2002 |
| JP | 2002-502698 | A | 1/2002 |
| JP | 2002-525577 | A | 8/2002 |
| JP | 2003090818 | A | 3/2003 |
| JP | 2003-517149 | A | 5/2003 |
| JP | 2003-523348 | A | 8/2003 |
| JP | 2003-342354 | A | 12/2003 |
| JP | 2005-512032 | A | 4/2005 |
| JP | 2005-513999 | A | 5/2005 |
| JP | 2005-521032 | A | 7/2005 |
| JP | 2005-264156 | A | 9/2005 |
| JP | 2005-530983 | A | 10/2005 |
| JP | 2007-504462 | A | 3/2007 |
| JP | 2008-170449 | A | 7/2008 |
| JP | 2009-075131 | A | 4/2009 |
| JP | 2009-534200 | A | 9/2009 |
| JP | 2010-507099 | A | 3/2010 |
| JP | 2010-215816 | A | 9/2010 |
| JP | 2011-017711 | A | 1/2011 |
| JP | 2011-519168 | A | 6/2011 |
| JP | 2011-234723 | A | 11/2011 |
| JP | 2012-163491 | A | 8/2012 |
| JP | 2012-518294 | A | 8/2012 |
| JP | 2012251921 | A | 12/2012 |
| WO | WO 94/28075 | A1 | 12/1994 |
| WO | WO 98/12539 | A1 | 3/1998 |
| WO | WO 99/41007 | A2 | 8/1999 |
| WO | WO 00/16089 | A2 | 3/2000 |
| WO | WO 01/43870 | A2 | 6/2001 |
| WO | WO 03/001889 | A2 | 1/2003 |
| WO | WO 03/023360 | A2 | 3/2003 |
| WO | WO 03/038033 | A2 | 5/2003 |
| WO | WO 2003/104273 | A2 | 12/2003 |
| WO | WO 2004/027093 | A1 | 4/2004 |
| WO | WO 2007/078868 | A1 | 7/2007 |
| WO | WO 2008/097370 | A2 | 8/2008 |
| WO | WO 2008/118167 | A1 | 10/2008 |
| WO | WO 2008/151146 | A2 | 12/2008 |
| WO | WO 2009/132321 | A1 | 10/2009 |
| WO | WO 2010/085763 | A1 | 7/2010 |
| WO | WO 2010/096593 | A2 | 8/2010 |
| WO | WO 2011/034620 | A2 | 3/2011 |
| WO | WO 2011/058136 | A1 | 5/2011 |
| WO | WO 2012/122929 | A1 | 9/2012 |
| WO | WO 2012/122959 | A1 | 9/2012 |
| WO | WO 2012/154594 | A1 | 11/2012 |
| WO | WO 2012/174479 | A1 | 12/2012 |
| WO | WO 2013/119845 | A1 | 8/2013 |
| WO | WO 2014/052989 | A2 | 4/2014 |

OTHER PUBLICATIONS

Canadian Office Action, Canadian Application No. 2,901,029, dated Sep. 8, 2015, 4 pages.

Carra, C. et al., "Proton-Coupled Electron Transfer in a Model for Tyrosine Oxidation in Photosystem II," Journal of the American Chemical Society, 2003, pp. 10429-10436, vol. 125.

Japanese Office Action, Japanese Application No. 2015-558184, dated Jan. 25, 2016, 4 pages.

PCT International Search Report, PCT/US2014/016737, dated Aug. 11, 2014, 13 Pages.

PCT International Preliminary Report on Patentability, PCT/US2014/016737, dated Feb. 24, 2015, 27 pages.

Camarero, J. A., "Review Article: Recent Developments in the Site-Specific Immobilization of Proteins Onto Solid Supports," Biopolymers (PeptideScience), 2008, pp. 450-458, vol. 90, No. 3.

"Compound Summary for: CID 44140593, Tris(2,2'-bipyridine)ruthenium(II) dichloride," PubChem Compound, 2009 [Retrieved from the Internet Jun. 29, 2014: <http://pubchem.ncbi.nlm.gov.summary/summary.cgi?cid=44140593&loc=ec_rcs>.

Sardesai, N. P., et al., "A Microfluidic Electrochemiluminescent Device for Detecting Cancer Biomarker Proteins," Anal Bioanal Chem., 2013, pp. 3831-3838; vol. 405, No. 11.

Uddayasankar, U., "Towards a Surface Microarray Based Multiplexed Immunoassay on a Digital Microfluidics Platform," 2010, pp. 1-69, Master of Science Thesis. [Retrieved from the Internet Jun. 29, 2014: <https://cipweb.cardinal-ip.com/PCTSRS/PCTSRS_DATA/PCT-US%2014-16737/PRIOR_ART_PCT-US_14-16737_Uddayasankar_Master_Thesis_2010.pdf>.

Canadian Office Action, Canadian Application No. 2,885,839, dated Jul. 22, 2016, 4 pages.

Canadian Office Action, Canadian Application No. 2,901,029, dated Dec. 2, 2016, 7 pages.

Wei, H. et al., "Electrochemiluminescence of tris(2,2'-bipyridyl)ruthenium and Its Applications in Bioanalysis: A Review," Luminescence, Mar.-Apr. 2011, pp. 77-85, vol. 26, Issue 2.

European Communication Under Rule 164(2)(A) EPC, European Application No. 13798499.3, dated Jun. 29, 2016, 4 pages.

European Examination Report, European Application No. 13783134.3, dated Jun. 29, 2016, 12 pages.

European Extended Search Report, European Application No. 14751871.6, dated Aug. 2, 2016, 6 pages.

European Examination Report, European Application No. 13798499.3, dated Sep. 23, 2016, 10 pages.

(56) References Cited

OTHER PUBLICATIONS

Lim, J-H. et al., "Direct-Write Dip-Pen Nanolithography of Proteins on Modified Silicon Oxide Surfaces," Angewandte Chemie International Edition, Wiley—VCH Verlag GmbH & Co., May 25, 2003, pp. 2309-2312, vol. 42, No. 20.
Canadian Office Action, Canadian Application No. 2,901,029, dated May 5, 2016, 7 pages.
Canadian Office Action, Canadian Application No. 2,891,651, dated Jun. 2, 2016, 5 pages.
Resch-Genger et al., "Quantum Dots Versus Organic Dyes as Fluorescent Labels," Nature Methods, Sep. 2008, pp. 763-775, vol. 5, No. 9.
Yuan, L., et al., "Integrated Tyramide and Polymerization-Assisted Signal Amplification for a Highly-Sensitive Immunoassay," Anal. Chem., 2012, pp. 10737-10744, vol. 84, No. 24.
Alawode, O. E. et al., "Clean Photodecompositionof 1-Methyl-4-Phenyl-1HTetrazole-5(4H)-Thiones to Carbodiimides Proceeds Via a Biradical," The Journal of Organic Chemistry, Jan. 7, 2011, pp. 216-222, vol. 76, No. 1.
Arimitsu Ket al., "Development of Highly Sensitive Photoreactive Materials Utilizing Photobase-generating Reactions and Base Proliferation Reactions", Journal of Synthetic Organic Chemistry Japan, Jan. 1, 2012, pp. 508-516, vol. 70(5), Yuki Gosei Kagaku Kaokai, Tokyo, JP (with English Abstract).
Beyer, M. et al., "Combinatorial Synthesis of Peptide Arrays Onto a Microchip," Science, Dec. 21, 2007, p. 1888, vol. 318, No. 5858.
Beyer et al. (Dec. 21, 2007) Science vol. 318 p. 1888 supporting online material, 6 pages.
Canadian First Office Action, Canadian Application No. 2,864,080, dated Nov. 19, 2015, 6 pages.
Canadian Second Office Action, Canadian Application No. 2,885,839, dated Apr. 20, 2017, 4 pages.
Canadian Second Office Action, Canadian Application No. 2,864,080, dated Dec. 1, 2016, 5 pages.
Canadian Second Office Action, Canadian Application No. 2,891,651, dated Feb. 10, 2017, 4 pages.
Canadian Office Action, Canadian Application No. 2,901,029, dated Jul. 5, 2017, 8 pages.
Canadian Office Action, Canadian Application No. 2,864,080, dated Jul. 10, 2017, 5 pages.
Canadian Office Action, Canadian Application No. 2,885,839, dated Sep. 15, 2017, 4 pages.
Canadian Office Action, Canadian Application No. 2,891,651, dated Sep. 15, 2017, 4 pages.
Canadian Office Action, Canadian Application No. 2,901,029, dated Mar. 21, 2018, 8 pages.
Canadian Office Action, Canadian Application No. 2,885,839, dated May 23, 2018, 3 pages.
European Second Examination Report, European Application No. 13798499.3, dated May 23, 2017, 6 pages.
European Examination Report, European Application No. 13783134.3, dated Apr. 1, 2016, 4 pages.
European Invitation to Pay Additional Search Fees, European Application No. 13783134.3, dated May 2, 2016, 4 pages.
European Extended Search Report, European Application No. 13747275.9, dated Sep. 25, 2015, 9 pages.
European Examination Report, European Application No. 14751871.6, dated Jul. 20, 2017, 5 pages.
European Examination Report, European Application No. 13747275.9, dated Sep. 21, 2017, 6 pages.
European Examination Report, European Application No. 13783134.3, dated Dec. 19, 2017, 5 pages.
Gundagola, A.S.V., Synthesis, Photochemistry, and DNA Photocleavage of Compounds Containing Tetrazolethione Scaffolds, Kansas State University, 2011, 3 pages, [Online] [Retrieved on May 1, 2015] Retrieved from the Internet<URL:http://krex.kstate.edu/dspace/handle/2097/12022>.
Han, S-Y. et al., "Recent Development of Peptide Coupling Reagents in Organic Synthesis," Tetrahedron, 2004, pp. 2447-2467, vol. 60.
Japanese Office Action, Japanese Application No. 2014-556684, dated Apr. 4, 2016, 5 pages.
Japanese Office Action, Japanese Application No. 2016-126181, dated May 22, 2017, 10 pages.
Japanese Office Action, Japanese Application No. 2016-148004, dated Jun. 21, 2017, 7 pages.
Japanese Office Action, Japanese Application No. 2015-534809, dated Aug. 28, 2017, 6 pages.
Lin et al., "Synthesis of Water Soluble Photoinitiators of Thioxanthone Derivatives III" Huadong Ligong Daxue Xuebao, Journal of East China University of Science and Technology, 2000, pp. 212-214, 220, vol. 26, No. 2 (with English abstract).
Meinl, E. et al., "Myelin Basic Protein-Specific T Lymphocyte Repertoire in Multiple Sclerosis, Complexity of the Response and Dominance of Nested Epitopes Due to Recruitment of Multiple T Cell Clones," The Journal of Clinical Investigation, Dec. 1993, pp. 2633-2643, vol. 92, No. 6.
Merrifield, R.B., "Solid Phase Peptide Synthesis. I. The Synthesis of a Tetrapeptide," J Am. Chem. Soc., Jul. 20, 1963, pp. 2149-2154, vol. 85, No. 14.
PCT International Search Report and Written Opinion, PCT Application No. PCT/US2013/062773, dated May 28, 2014, 20 pages.
PCT Invitation to Pay Additional Fees, PCT Application No. PCT/US2013/062773, dated Mar. 7, 2014, 9 pages.
PCT International Preliminary Report on Patentability for PCT International Application No. PCT/US13/62773, dated Dec. 18, 2014, 7 pages.
PCT International Search Report and Written Opinion, PCT Application No. PCT/US2013/070207, dated Jun. 23, 2014, 19 pages.
PCT Invitation to Pay Additional Fees, PCT Application No. PCT/US2013/070207, dated Mar. 14, 2014, 8 pages.
PCT Written Opinion for PCT International Application No. PCT/US2013/070207, dated Feb. 12, 2015, 13 pages.
PCT International Preliminary Report on Patentability for PCT International Application No. PCT/US2013/070207, dated Mar. 30, 2015, 12 pages.
PCT Invitation to Pay Additional Fees, PCT Application No. PCT/US14/16737, dated May 19, 2014, 2 pages.
PCT International Search Report and Written Opinion, PCT Application No. PCT/US13/25190, dated Jun. 26, 2013, 22 pages.
PCT Invitation to Pay Additional Fees, PCT Application No. PCT/US13/25190, dated May 1, 2013, 4 pages.
PCT International Preliminary Report on Patentability for PCT International Application No. PCT/US13/25190, dated Apr. 4, 2014, 18 pages.
PCT International Search Report and Written Opinion, PCT Application No. PCT/US15/17173, dated Jun. 3, 2015, 16 pages.
PCT International Search Report and Written Opinion, PCT Application No. PCT/US15/49528, dated Feb. 1, 2016, 18 pages.
PCT Invitation to Pay Additional Fees, PCT Application No. PCT/US15/49528, dated Nov. 20, 2015, 3 pages.
Pellois, J.P. et al., "Individually Addressable Parallel Peptide Synthesis on Microchips". Nature Biotechnology, Sep. 2002, pp. 922-926, vol. 20, No. 9.
"Proteomics 2010: Solid-Phase Peptide Synthesis (SPPS) and Applications of Synthetic Peptides," Jan. 2010, 63 pages [Online] [Retrieved on Sep. 16, 2015] Retrieved from the Internet<URL:http://bas.niu.edu.tw/download.php?filename=12155_cf09f16c. ppt&dir=communicty_forum/31&title=Topic+10-SPPS>.
Shin et al., "Automated Maskless Photolithography System for Peptide Microarray Synthesis on a Chip," J. Comb. Chem., 2010, pp. 463-471, vol. 12, No. 4.
Sun X. et al., "Bicyclic Guanidinium Tetraphenylborate: A Photobase Generator and a Photocatalyst for living Anionic Ring-Opening Polymerization and Cross-Linking of Polymeric Materials Containing Ester and Hydroxy Groups" Journal of The American Chemical Society, Jul. 1, 2008, pp. 8130-8131, vol. 130(26).
Suyama K. et al., "Photobase Generators: Recent Progress and Application Trend in Polymer Systems", Progress in Polymer Science, Feb. 1, 2009, pp. 194-209, vol. 34(2), Pergamon Press, Oxford, GB.

(56) References Cited

OTHER PUBLICATIONS

Tapia, V. et al., "Evaluating the Coupling Efficiency of Phosphorylated Amino Acids for SPOT Synthesis," J. Peptide Sci., 2008, pp. 1309-1314, vol. 14, No. 12.
United States Office Action, U.S. Appl. No. 15/216,267, dated Oct. 26, 2017, seven pages.
United States Office Action, U.S. Appl. No. 14/672,123, dated Dec. 21, 2015, 10 pages.
United States Office Action, U.S. Appl. No. 14/454,554, dated Mar. 16, 2015, 14 pages.
United States Office Action, U.S. Appl. No. 14/432,200, dated Jul. 19, 2017, 17 pages.
United States Office Action, U.S. Appl. No. 14/432,200, dated Feb. 8, 2017, 22 pages.
United States Office Action, U.S. Appl. No. 14/768,196, dated Sep. 22, 2017, 18 pages.
Wagner, "Quality Control for Peptide Chip Array Production," PhD Thesis, 2011, 140 pages, [Online] [Retrieved on Jun. 14, 2013] Retrieved from the Internet<URL:http://archiv.ub.uni-heidelberg.de/volltextserver/12602/1/report.pdf>.
Wang et al, Microfluidic DNA microarray analysis: A review, 2011, Analytica Chimica Acta, 687, 12-27.
Young, J.D. et al., "Coupling Efficiencies of Amino Acids in the Solid Phase Synthesis of Peptides," Peptide Research, Jul. 1990, pp. 194-200, vol. 3, No. 4.
Zhao, Y. et al., "A Fluorescent Amino Acid Probe to Monitor Efficiency of Peptide Conjugation to Glass Surfaces for High Density Microarrays," Mol. Biosyst., Epub Jan. 13, 2012, pp. 879-887, vol. 8, No. 3.
Erber et al., "An enhanced immunocytochemical method for staining bone marrow trephine sections." Journal of clinical pathology 50, No. 5 (1997): 389-393.

* cited by examiner

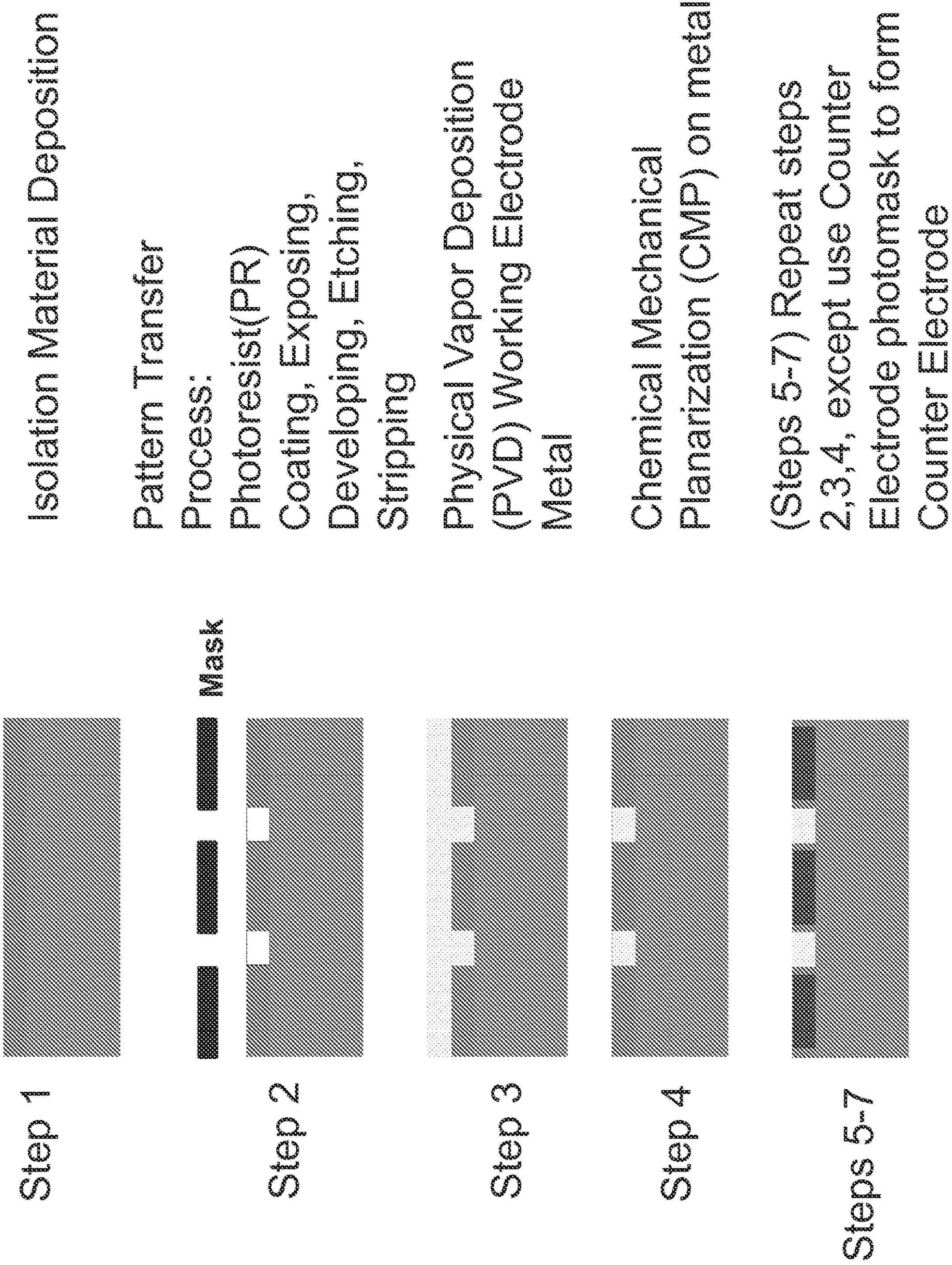
AECL Chip Manufacturing Process
Fig. 10 A
Step 1
Isolation Material Deposition
Step 2
Mask
Pattern Transfer Process: Photoresist(PR) Coating, Exposing, Developing, Etching, Stripping
Step 3
Physical Vapor Deposition (PVD) Working Electrode Metal
Step 4
Chemical Mechanical Planarization (CMP) on metal
Steps 5-7
(Steps 5-7) Repeat steps 2,3,4, except use Counter Electrode photomask to form Counter Electrode

AECL Chip Manufacturing Process (cont.)

AECL Pillar Preparation

AECL Pillar (Top View)

METHODS AND COMPOSITIONS FOR AMPLIFIED ELECTROCHEMILUMINESCENCE DETECTION

CROSS REFERENCE TO RELATED APPLICATIONS

This application is the National Stage of International Application No. PCT/US2014/016737, filed Feb. 17, 2014, which claims the benefit of U.S. Provisional Application Ser. No. 61/765,584, filed Feb. 15, 2013, which are hereby incorporated in their entirety by reference.

BACKGROUND

A typical microarray system generally comprises biomolecular probes, such as DNA, proteins, or peptides, formatted on a solid planar surface like glass, plastic, or silicon chip, plus the instruments needed to handle samples (automated robotics), to read the reporter molecules (scanners) and analyze the data (bioinformatic tools). Microarray technology can facilitate monitoring of many probes per square centimeter. Advantages of using multiple probes include, but are not limited to, speed, adaptability, comprehensiveness and the relatively cheaper cost of high volume manufacturing. The uses of such an array include, but are not limited to, diagnostic microbiology, including the detection and identification of pathogens, investigation of anti-microbial resistance, epidemiological strain typing, investigation of oncogenes, analysis of microbial infections using host genomic expression, and polymorphism profiles.

Electrochemiluminescence or electrogenerated chemiluminescence (ECL) is a kind of luminescence produced during electrochemical reactions in solutions. In electrogenerated chemiluminescence, electrochemically generated intermediates undergo a highly exergonic reaction to produce an electronically excited state that then emits light upon relaxation to a lower-level state. This wavelength of the emitted photon of light corresponds to the energy gap between these two states. ECL excitation can be caused by energetic electron transfer (redox) reactions of electrogenerated species. Such luminescence excitation is a form of chemiluminescence where one/all reactants are produced electrochemically on the electrodes.

ECL is usually observed during application of potential (several volts) to electrodes of electrochemical cell that contains solution of luminescent species (polycyclic aromatic hydrocarbons, metal complexes, Quantum Dots or Nanoparticles) in aprotic organic solvent (ECL composition). In organic solvents both oxidized and reduced forms of luminescent species can be produced at different electrodes simultaneously or at a single one by sweeping its potential between oxidation and reduction. The excitation energy is obtained from recombination of oxidized and reduced species.

In aqueous medium which is mostly used for analytical applications simultaneous oxidation and reduction of luminescent species is difficult to achieve due to electrochemical splitting of water itself so the ECL reaction with the coreactants is used. In the later case luminescent species are oxidized at the electrode together with the coreactant which gives a strong reducing agent after some chemical transformations (the oxidative reduction mechanism).

There is a need for a platform which can simultaneously detect multiple analytes of varying concentrations, Typical ELISA based assays have 4 orders of magnitude and hence is restricted in detecting multiple analytes varying from ug/ml to fg/ml. Recent advances in electrochemiluminescence have pushed the limits of detection to pg/ml with a dynamic range up to 4-5 orders in log scale. However, simultaneous detection of multiple analytes in varying concentration of 6 or more magnitudes has not been possible due to limitation on the tags used for electrochemiluminescence.

SUMMARY

The invention encompasses, in several aspects formulations, substrates, and arrays. The invention also includes methods of detecting analytes using the formulations, substrates, and arrays.

In an aspect, the invention comprises methods of detecting a target biomolecule comprising contacting sample comprising said target biomolecule with a capture ligand, said capture ligand being immobilized at a defined location on a substrate and capable of specifically binding said target biomolecule thereby immobilizing said target biomolecule at said defined location on said substrate; contacting said immobilized target biomolecule with a detection ligand, said detection ligand capable of specifically binding to said immobilized target biomolecule and having peroxidase activity thereby forming an immobilized target biomolecule-detection ligand complex; contacting said complex with a tagging solution comprising an AECL tag under conditions that promote covalent binding of a plurality of AECL tags to said complex; washing said substrate to remove unbound AECL tag from said substrate; contacting said substrate with a detection solution that reacts with said bound AECL tag to generate luminescence when a voltage is applied to said defined location on said substrate; applying said voltage to said defined location on said substrate; and measuring luminescence from said defined location on said substrate thereby detecting said target biomolecule.

In certain embodiments, the defined location on the substrate is a microarray feature or a plurality of microarray features. In certain embodiments, the features can have an edge dimension between 50 nm and 1 um, or between 50 nm and 100 nm or between 50 nm and 75 nm. In certain embodiments, the capture ligands are covalently bound to the defined location via a COOH or an NH2 moiety provided on the substrate.

In certain embodiments, the capture ligand and detection ligand comprise antibodies, peptides, proteins, or antigen binding proteins.

In certain embodiments, the sample can comprise blood, serum, plasma, saliva, urine, feces or cerebrospinal fluid (CSF).

In certain embodiments, the sample is obtained from a human subject.

In certain embodiments, the AECL tag comprises a metal chelate, a rare earth metal chelate, a ruthenium chelate, or tris (bipyridine)ruthenium(II). The AECL tag can further comprise tyramide bound to the metal chelate. In certain embodiments the AECL tag comprises

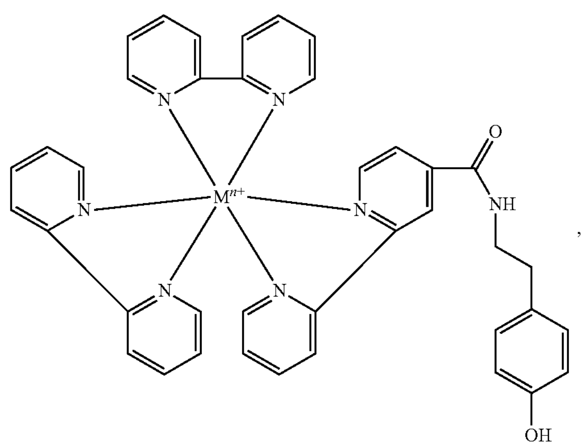

wherein $M^{n+}$ is $Ru^{2+}$.

In certain embodiments, the invention includes AECL tag compositions as well as kits and solutions for binding said AECL tag compositions to target biomolecules and detecting their binding via an emitted luminescent signal.

In other embodiments, the invention includes solid state microarrays and pillar assemblies for mounting the microarrays and performing AECL assays. In certain embodiments, the solid state microarrays comprise chemically-functionalized surfaces comprising COOH or NH2 functional groups that can be covalently bound to capture ligands.

In some embodiments, the solid state microarrays of the present invention have an electrical potential difference between at least one pair of working and counter electrodes that generates electrochemiluminescence from bound AECL tags.

In some embodiments, the solid state microarrays comprise at least 2, 4, 8, 16, 32, 64, 100, 200, 500, 1000, 2000, 5000, 10,000, 15,000, 20,000, 30,000, 40,000, 50,000, 60,000, 70,000, 80,000, 90,000, 1,000,000, 1,500,000, 2,000,000 or more working electrodes.

In some aspects, the invention includes an assay plate for mounting a solid state microarray. The assay plate includes a pillar that includes a top surface and a bottom surface. The top surface includes a mounting surface to receive a solid state microarray of the invention as well as at least one working electrode and one counter electrode configured to contact and to be in electrical communication with a corresponding at least one working electrode and counter electrode on a bottom surface of the solid state microarray. The bottom surface of the pillar includes contacts for supplying power to the at least one pillar working electrode and pillar counter electrode. In some embodiments, the assay plate includes a plurality of pillars, such as 24, 96, 384 or 1586 pillars. In some embodiments, the pillars comprise at least 2, 4, 8, 16, 32, 64, 100, 200, 500, 1000, 2000, 5000, 10,000, 15,000, 20,000, 30,000, 40,000, 50,000, 60,000, 70,000, 80,000, 90,000, 1,000,000, 1,500,000, 2,000,000 or more working electrodes.

In some embodiments, the invention includes an assembly that includes an assay plate with a microarray mounted on the surface of the assay plate pillar such that the corresponding pillar and microarray working and counter electrodes are in electrical contact. In yet other embodiments, the assemblies of the invention further include an assay cap, that provides pillar walls mounted on struts that slidably engage grooves on the pillar mounts. When the cap and the assay plate are engaged, the pillar walls provide barriers for a reservoir that can hold assay fluid in contact with the microarray.

In yet other embodiments, the AECL assays of the invention have improved detection limits, such that concentrations of target biomolecules in a sample can be detected at limits on the order of 100 fg/mL, 10 fg/mL, or 1 fg/mL.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Figure 1:
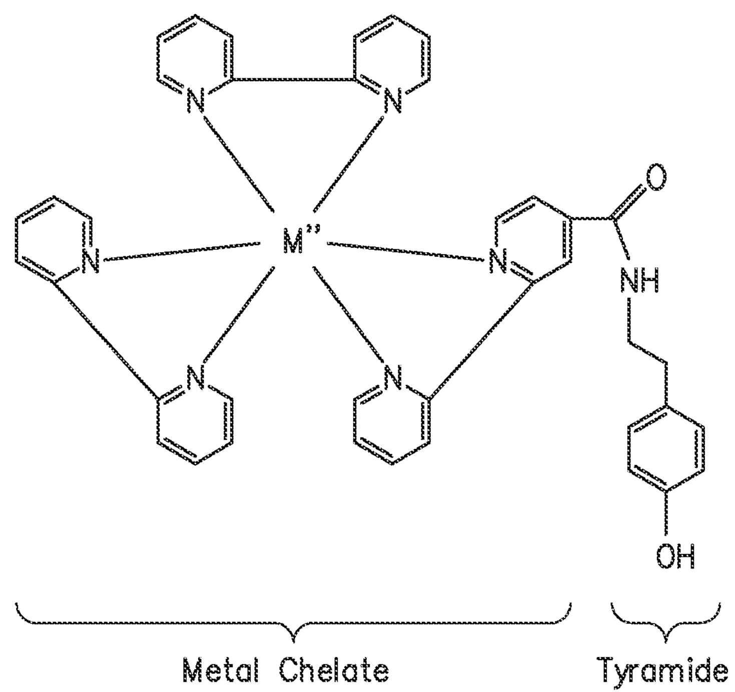
FIG. 1 shows the structure of an embodiment of an amplified electrochemiluminescent (AECL) tag comprising a metal chelate ester attached to tyramide.

Terms used in the claims and specification are defined as set forth below unless otherwise specified.

As used herein the term "wafer" refers to a slice of semiconductor material, such as silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 μm to 775 μm.

As used herein the terms "biomolecule," "polypeptide," "peptide," or "protein" are used interchangeably to describe a chain or polymer of amino acids that are linked together by bonds. Accordingly, the term "peptide" as used herein includes a dipeptide, tripeptide, oligopeptide, and polypeptide. The term "peptide" is not limited to any particular number of amino acids. In some aspects, a peptide contains about 2 to about 50 amino acids, about 5 to about 40 amino acids, or about 5 to about 20 amino acids. A molecule, such as a protein or polypeptide, including an enzyme, can be a "native" or "wild-type" molecule, meaning that it occurs naturally in nature; or it may be a "mutant," "variant," "derivative," or "modification," meaning that it has been made, altered, derived, or is in some way different or changed from a native molecule or from another molecule such as a mutant.

As used herein the term "microarray" refers to a substrate on which different probe molecules of proteins (e.g., antibodies, antibody fragments, or other polypeptide sequences) or specific DNA binding sequences have been affixed at separate locations in an ordered manner thus forming a microscopic array. Specific probes are present in large copy number (e.g., 10ˆ6) within an array unit called a feature. An array can be characterized by the feature density (e.g., # features/cmˆ2), the total number of features, the length of a feature edge, a feature area, or the separation between features (sometimes referred to as the array's "pitch").

As used herein the term "microarray system" refers to a system usually comprised of biomolecular probes formatted on a solid planar surface like glass, plastic or silicon chip plus the instruments needed to handle samples (automated robotics), to read the reporter molecules (scanners) and analyze the data (bioinformatic tools).

As used herein, the terms "immunological binding" and "immunological binding properties" refer to the type of non-covalent interactions that occurs between an immunoglobulin molecule (or variant thereof such as an scFv) and an antigen for which the immunoglobulin is specific.

As used herein the term "biological sample" refers to a sample derived from biological tissue or fluid that can be assayed for an analyte(s) of interest. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect analyte(s) of interest in samples from any organism (e.g., mammal, bacteria, virus, algae, or yeast) or mammal, such as dogs, cats, sheep, cattle, and pigs. The sample may be pretreated as necessary by dilution in an appropriate buffer solution or concentrated, if desired.

As used herein, the term "assay" refers to a type of biochemical test that measures the presence or concentration of a substance of interest in solutions that can contain a complex mixture of substances.

The term "subject" as used herein may refer to a human or any other animal having a disorder for testing, diagnosis or treatment.

The term "antigen" as used herein refers to a molecule that triggers an immune response by the immune system of a subject, e.g., the production of an antibody by the immune system and/or activation of the cellular arm of the immune system (e.g., activation of phagocytes, natural killer cells, and antigen-specific cytotoxic T-lymphocytes, along with release of various cytokines in response to an antigen). Antigens can be exogenous, endogenous or auto antigens. Exogenous antigens are those that have entered the body from outside through inhalation, ingestion or injection. Endogenous antigens are those that have been generated within previously-normal cells as a result of normal cell metabolism, or because of viral or intracellular bacterial infection. Auto antigens are those that are normal protein or protein complex present in the host body but can stimulate an immune response.

As used herein the term "epitope" or "immunoactive regions" refers to distinct molecular surface features of an antigen capable of being bound by component of the adaptive immune system, e.g., an antibody or T cell receptor. Antigenic molecules can present several surface features that can act as points of interaction for specific antibodies. Any such distinct molecular feature can constitute an epitope. Therefore, antigens have the potential to be bound by several distinct antibodies, each of which is specific to a particular epitope.

As used herein the term "antibody" or "immunoglobulin molecule" refers to a molecule naturally secreted by a particular type of cells of the immune system: B cells. There are five different, naturally occurring isotypes of antibodies, namely: IgA, IgM, IgG, IgD, and IgE.

As used herein the term "immune-related molecule" refers to a biological molecule involved in the activation or regulation of an immune response. These include, for example, an antibody, T cell receptor, or MHC complex (e.g., human leukocyte antigen).

As used herein, the term "inflammatory response molecule" refers to molecules that signal or mediate an inflammatory response, e.g., cytokines such as interleukin and tumor necrosis factor. Inflammatory response molecules include, for example, pro-inflammatory molecules.

As used herein, the term "autoimmune disorder" refers to any of a large group of diseases characterized by abnormal functioning of the immune system that causes a subject's immune system to damage the subject's own tissues. Celiac disorder, lupus erythematosis, and rheumatoid arthritis are examples of autoimmune disorders. Autoimmune disorders may be induced by environmental factors.

The term "percent identity" or "percent sequence identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

It must be noted that, as used in the specification and the appended claims, the singular forms "a," "an," and "the" include plural referents unless the context clearly dictates otherwise.

Compositions

AECL Tales and Secondary Antibody.

Also disclosed herein are compositions for amplified electrochemiluminescent detection of biomolecules of interest on an array. In an embodiment, a compound is provided that covalently links an electrochemiluminescence (ECL) moiety with a signal amplification moiety to generate an amplified electrochemiluminescence (AECL) tag. FIG. 1. The AECL tag generates detectable electromagnetic radiation (i.e., light) upon exposure to voltage in the presence of tripropyl amine (TPA). In an embodiment, the ECL moiety is a metal chelate ester. In an embodiment, the metal is a rare earth metal. In an embodiment the rare earth metal is Ruthenium (Ru). In an embodiment, the signal amplification moiety is tyramide. The use of the tyramide as part of the AECL tag provides for a minimal background. The AECL tag is used with an enzyme-conjugated antigen binding protein (e.g., an HRP-conjugated antibody) resulting in highly localized enzyme-mediated AECL tag deposition to improve detection of bound target molecules. See FIG. 4 and accompanying description below.

Figure 2:
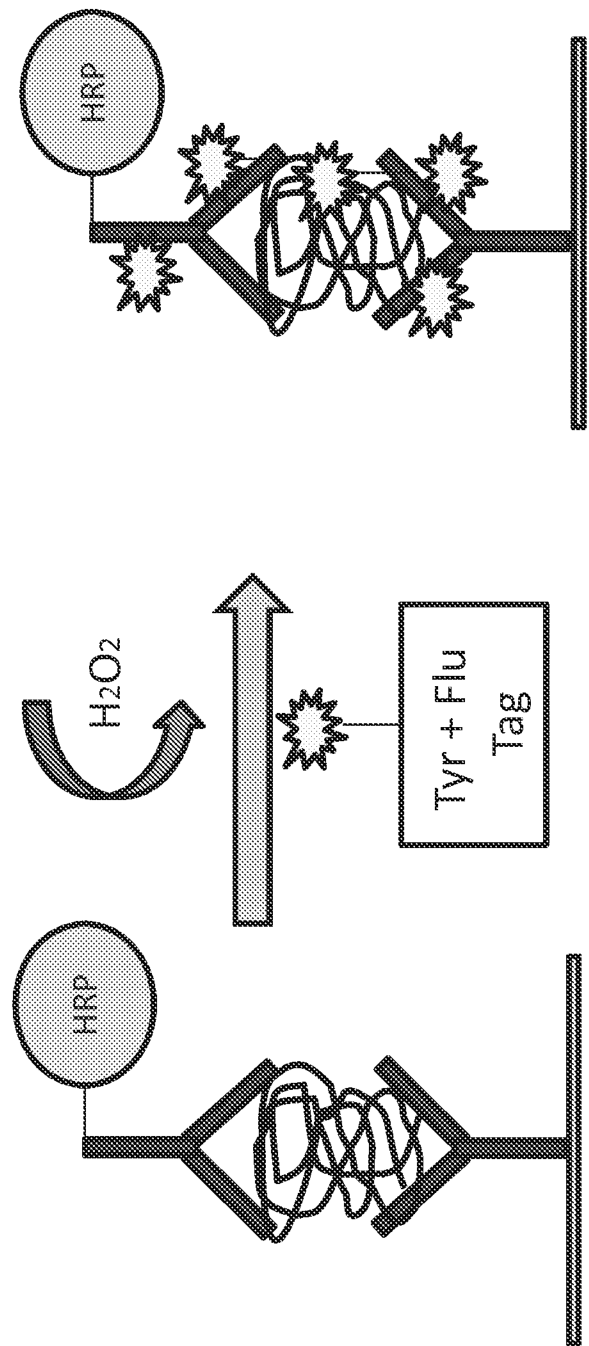
FIG. 2 shows the prior art process of tyramide signal amplification catalyzed by horseradish peroxidase (HRP) attached to an antibody. The tyramide is bound to a fluorescent marker. The HRP localized to the secondary antibody catalyzes the binding of tyramide to electron rich moieties (predominantly tyrosine residues) in a target.

Prior art tyramide signal amplification assays result in covalent binding of labeled tyramide to tyrosine residues (e.g., on the secondary antibody, target biomolecule and primary antibody) in the presence of horseradish peroxidase (HRP) and hydrogen peroxide. The label can be a fluorescent tag, or a detectable reaction product e.g., an insoluble product produced by action of another enzyme such as alkaline phosphatase on a chromogenic substrate. See FIG. 2.

Figure 3:
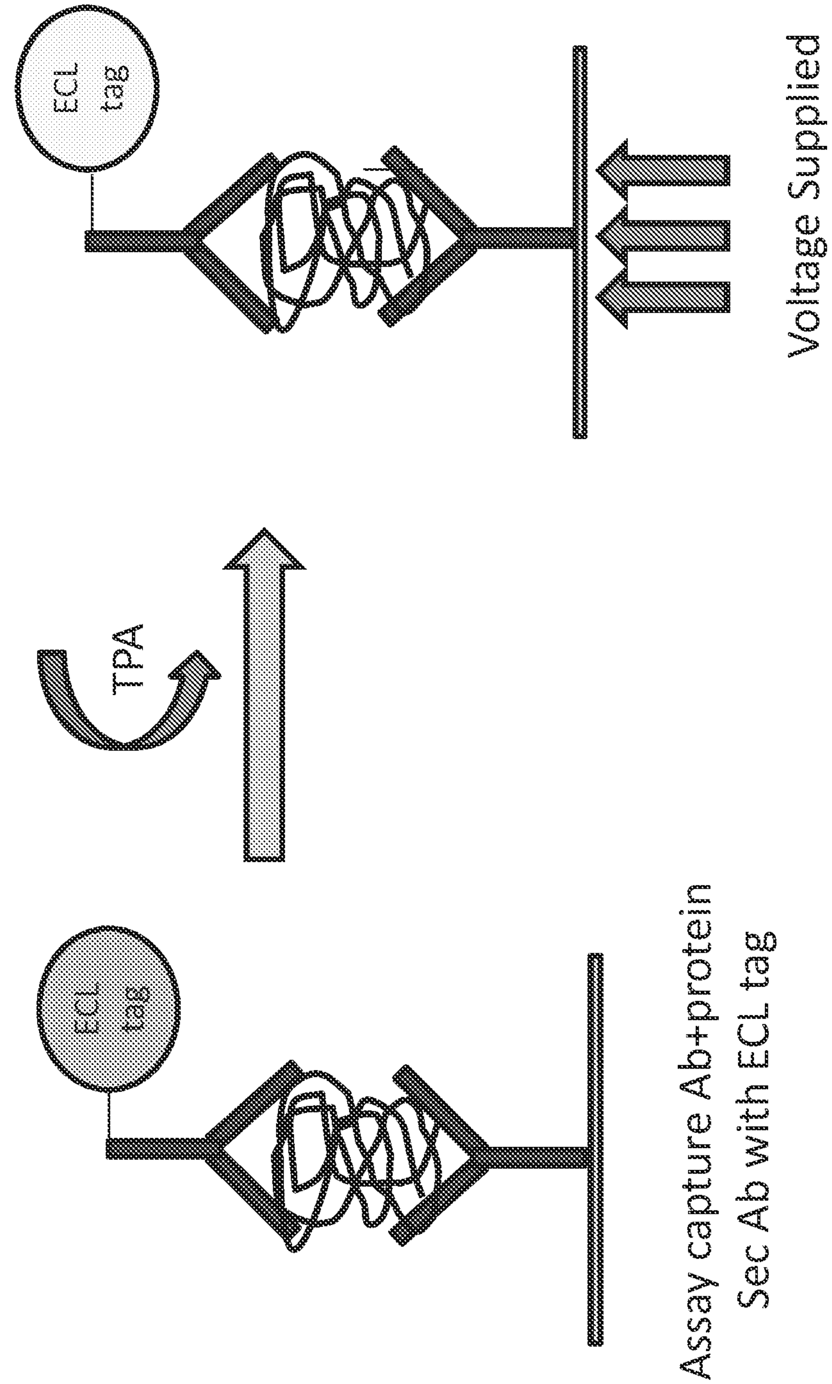
FIG. 3 shows a prior art sandwich ELISA to detect a captured target biomolecule using an ECL-tagged secondary antibody and application of voltage in the presence of tripropyl amine (TPA) to produce a detectable light signal that can be used to quantitate captured target biomolecule.

Prior art ECL assays use an ECL tag comprising a metal chelate ester covalently bound to a detection ligand such as, e.g., a secondary antibody used in a sandwich ELISA format. The ECL tag emits light in the presence of tripropyl amine (TPA) when exposed to an electric field (e.g., by supplying a voltage difference across a working electrode in electrical communication with a binding complex comprising the captured target biomolecule and a counter electrode), a phenomena called electrochemiluminescence (FIG. 3).

Figure 4:
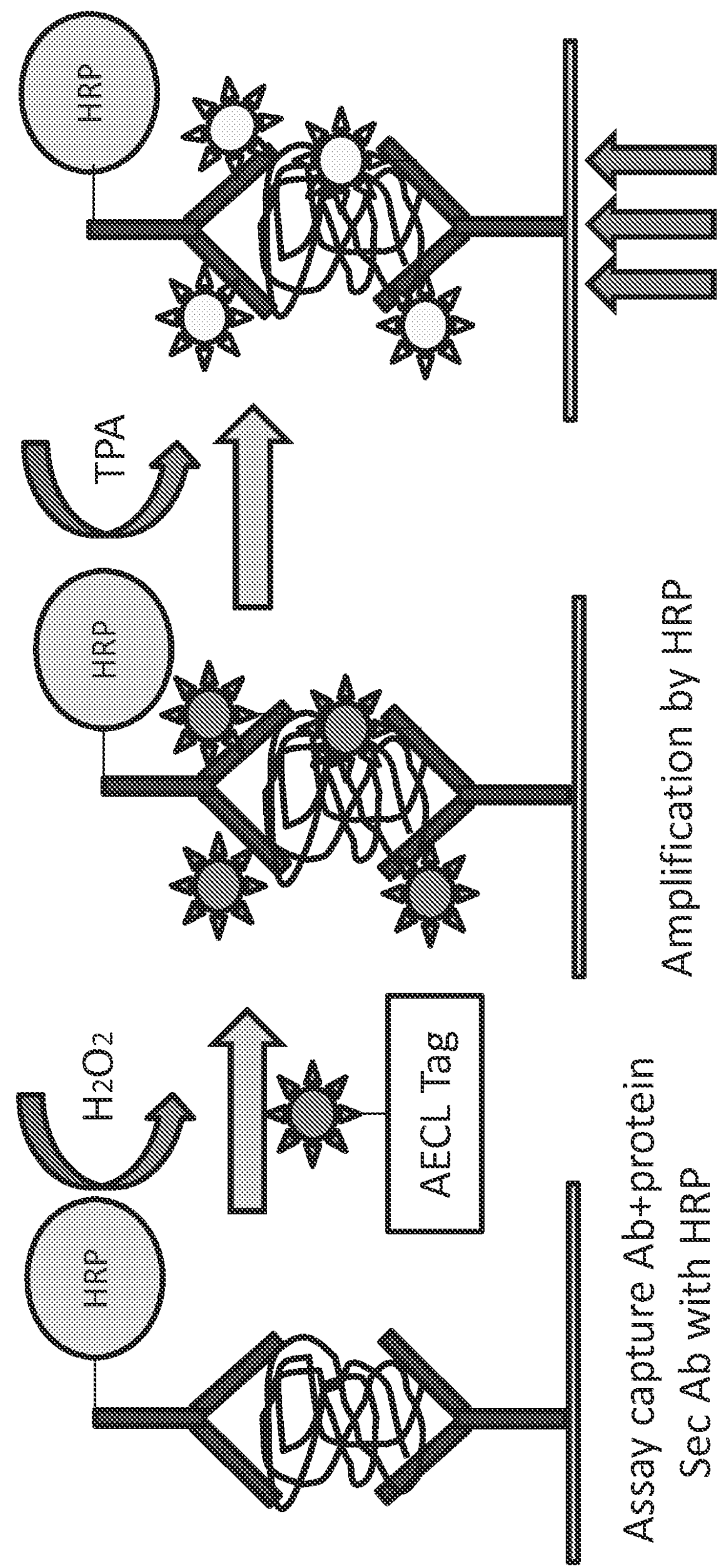
FIG. 4 illustrates a sandwich ELISA embodiment of the present invention to detect a captured target biomolecule using a secondary antibody—horseradish peroxidase (HRP) conjugate. Upon addition of an AECL tag in the presence of hydrogen peroxide, the HRP catalyzes attachment of the AECL tag's tyramide moiety to electron rich targets (predominantly tyrosine residues) that are proximate to the bound secondary antibody, thus labeling the captured target biomolecule complex with multiple AECL tags. Application of voltage in the presence of TPA produces an amplified light signal that can be used to quantitate captured target biomolecule.

In some embodiments of the present invention, an antibody array is exposed to a sample comprising a biomolecule of interest. At least one primary antibody bound to the array surface binds to the biomolecule of interest. After washing the array, the array is exposed to a solution of secondary antibody conjugated to horseradish peroxidase (HRP), wherein the secondary antibody binds to the biomolecule of interest. After washing, the array is exposed to a solution comprising hydrogen peroxide and an AECL tag. AECL tags bind to complexes attached to the array which comprise primary antibodies bound to protein and secondary antibody conjugated to HRP. The AECL tags comprise tyramide which binds to tyrosine in the presence of HRP (conjugated to the secondary antibody). The array is then washed and exposed to tripropylamine (TPA), which reacts with the metal chelate of the AECL tag to activate it, thus causing it to generate chemiluminescence when exposed to a voltage potential (e.g., a voltage potential from the array). Thus, under applied voltage, the metal chelate ester generates an electrochemiluminescent (ECL) output (FIG. 4). This method of AECL tagging improves the detection sensitivity by at least 10 fold to 1000 fold as compared to commercially available ECL.

Substrates

Also disclosed herein are substrates. In some aspects a substrate surface is planar (i.e., 2-dimensional). In some aspects a substrate surface is functionalized with free carboxylic acid groups. In some aspects, a substrate surface is functionalized with free amine groups. A surface that is functionalized with free amine groups may be converted to free carboxylic acid groups by reacting with activating the carboxylic acid groups of a molecule comprising at least two free carboxylic acid groups (e.g., converting the carboxylic acid group to a carbonyl group using carbodiimide) and reacting the molecule with the free amine groups attached to the surface of the substrate. In some embodiments, the molecule comprising multiple carboxylic acid groups is succinic anhydride, polyethylene glycol diacid, benzene-1,3,5-tricarboxylic acid, benzenehexacarboxylic acid, or carboxymethyl dextran.

In some aspects, a substrate can include a porous layer (i.e., a 3-dimensional layer) comprising functional groups for binding a first monomer building block. In some aspects, a substrate surface comprises pillars for peptide attachment or synthesis. In some embodiments, a porous layer is added to the top of the pillars.

Porous Layer Substrates

Porous layers which can be used are flat, permeable, polymeric materials of porous structure which have a carboxylic acid functional group (which is native to the constituent polymer or which is introduced to the porous layer) for attachment of the first peptide building block. For example, a porous layer can be comprised of porous silicon with functional groups for attachment of a polymer building block attached to the surface of the porous silicon. In another example, a porous layer may comprise a cross-linked polymeric material. In some embodiments, the porous layer may employ polystyrenes, saccharose, dextrans, polyacryloylmorpholine, polyacrylates, polymethylacrylates, polyacrylamides, polyacrylolpyrrolidone, polyvinylacetates, polyethyleneglycol, agaroses, sepharose, other conventional chromatography type materials and derivatives and mixtures thereof. In some embodiments, the porous layer building material is selected from: poly(vinyl alcohol), dextran, sodium alginate, poly(aspartic acid), poly(ethylene glycol), poly(ethylene oxide), poly(vinyl pyrrolidone), poly(acrylic acid), poly(acrylic acid)-sodium salt, poly(acrylamide), poly (N-isopropyl acrylamide), poly(hydroxyethyl acrylate), poly (acrylic acid), poly(sodium styrene sulfonate), poly(2-acrylamido-2-methyl-1-propanesulfonic acid), polysaccharides, and cellulose derivatives. Preferably the porous layer has a porosity of 10-80%. In an embodiment, the thickness of the porous layer ranges from 0.01 μm to about 1,000 μm. Pore sizes included in the porous layer may range from 2 nm to about 100 μm.

According to another aspect of the present invention there is provided a substrate comprising a porous polymeric material having a porosity from 10-80%, wherein reactive groups are chemically bound to the pore surfaces and are adapted in use to interact, e.g. by binding chemically, with a reactive species, e.g., deprotected monomeric building blocks or polymeric chains. In an embodiment the reactive group is a carboxylic acid group. The carboxylic acid group is free to bind, for example, an unprotected amine group of a peptide or polypeptide.

In an embodiment, the porous layer is in contact with a support layer. The support layer comprises, for example, metal, plastic, silicon, silicon oxide, or silicon nitride. In another embodiment, the porous layer may be in contact with a patterned surface, such as on top of pillar substrates described below.

AECL Chip Substrates

Semiconductor manufacturing processes can be used to generate AECL chips that have solid state electrode circuitry built into one surface of a silicon substrate and biomolecular features present, usually patterned as an array on the opposite face of the substrate on the working electrode surface. Any technique useful for patterning biomolecular features such as peptides or proteins can be used, including those for synthesizing peptides in situ in an N→C or C→N configuration, or for tethering whole proteins at defined locations using carbodiimide based chemistries such as those described in co-owned cases WO2013/119845 and PCT/US2013/070207, and described below.

The AECL chip manufacturing process results in production of an integrated biochip sensor device that is attached to a controller used to drive voltage feeds to reference and working electrodes in order to excite a chemiluminescent signal, which, according to embodiments of the present invention, is amplified.

The controller can also be programmed and used to drive image acquisition and data storage for the assay results. Additional details relating to AECL chip substrate manufacture and the use of the resulting chips in AECL assays is described in greater detail in Examples 1-6, below.

Arrays

Also disclosed herein are arrays. In some aspects, the surface of the array is functionalized with free carboxylic acids. In some aspects, the free carboxylic acids are activated to bind to amine groups, e.g., during polypeptide synthesis on the surface of the array. In some embodiments, the surface density of free carboxylic acid groups on the array is greater than $10/cm^2$, $100/cm^2$, $1,000/cm^2$, $10,000/cm^2$, $100,000/cm^2$, $1,000,000/cm^2$, or $10,000,000/cm^2$.

In some aspects, an array can be a three-dimensional array, e.g., a porous array comprising features attached to the surface of the porous array. In some aspects, the surface of a porous array includes external surfaces and surfaces defining pore volume within the porous array. In some aspects, a three-dimensional array can include features attached to a surface at positionally-defined locations, said features each comprising: a collection of peptide chains of determinable sequence and intended length. In an embodiment, within an individual feature, the fraction of peptide chains within said collection having the intended length is characterized by an average coupling efficiency for each coupling step of greater than 98%.

In some aspects, the average coupling efficiency for each coupling step is at least 98.5%. In some aspects, the average coupling efficiency for each coupling step is at least 99%. In some aspects, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%.

In some aspects, each peptide chain is from 5 to 60 amino acids in length. In some aspects, each peptide chain is at least 5 amino acids in length. In some aspects, each peptide chain is at least 5, 10, 15, 20, 25, 30, 35, 40, 45, 50, 55, or 60 amino acids in length. In some aspects, each peptide chain is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some aspects, each peptide chain comprises one or more L amino acids. In some aspects, each peptide chain comprises one or more D amino acids. In some aspects, each peptide chain comprises one or more naturally occurring amino acids. In some aspects, each peptide chain comprises one or more synthetic amino acids.

In some aspects, an array can include at least 1,000 different peptide chains attached to the surface. In some aspects, an array can include at least 10,000 different peptide chains attached to the surface. In some aspects, an array can include at least 100, 500, 1000, 2000, 3000, 4000, 5000, 6000, 7000, 8000, 9000, 10,000, or greater than 10,000 different peptide chains attached to the surface (or any integer in between).

In some aspects, each of the positionally-defined locations is at a different, known location that is physically separated from each of the other positionally-defined locations. In some aspects, each of the positionally-defined locations is a positionally-distinguishable location. In some aspects, each determinable sequence is a known sequence. In some aspects, each determinable sequence is a distinct sequence.

In some aspects, the features are covalently attached to the surface. In some aspects, said peptide chains are attached to the surface through a linker molecule or a coupling molecule.

In some aspects, the features comprise a plurality of distinct, nested, overlapping peptide chains comprising subsequences derived from a source protein having a known sequence. In some aspects, each peptide chain in the plurality is substantially the same length. In some aspects, each peptide chain in the plurality is the same length. In some aspects, each peptide chain in the plurality is at least 5 amino acids in length. In some aspects, each peptide chain in the plurality is at least 5, 10, 15, 20, 25, 30, 35, 40, 45, 50, 55, or 60 amino acids in length. In some aspects, each peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some aspects, at least one peptide chain in the plurality is at least 5 amino acids in length. In some aspects, at least one peptide chain in the plurality is at least 5, 10, 15, 20, 25, 30, 35, 40, 45, 50, 55, or 60 amino acids in length. In some aspects, at least one peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some aspects, each polypeptide in a feature is substantially the same length. In some aspects, each polypeptide in a feature is the same length. In some aspects, the features comprise a plurality of peptide chains each having a random, determinable sequence of amino acids.

Carboxylic Acid Activation Solutions

Disclosed herein are activation formulations for activating carboxylic acid so that it reacts with a free amino group of a biomolecule, e.g., a peptide. An activation formulation can include components such as a carboxylic acid group activating compound and a solvent. In an embodiment, the carboxylic acid group activating compound is a carbodiimide or a carbodiimide precursor. In some aspects, the carbodiimide is 1-ethyl-3-(3-dimethylaminopropyl) carbodiimide. In some embodiments, the carboxylic acid group activating compound is N-Hydroxysuccinimide (NHS). In some embodiments, the carboxylic acid group activating compound is selected from: 1-Ethyl-3-(3-dimethylaminopropyl)carbodiimide [EDC], N-hydroxysuccinimide [NHS], 1,3-Diisopropylcarbodiimide [DIC], hydroxybenzotriazole (HOBt), (O-(7-azabenzotriazol-1-yl)-N,N,N',N'-tetramethyluronium hexafluorophosphate) [HATU], benzotriazol-1-yl-oxytripyrrolidinophosphonium hexafluorophosphate [PyBOP], and N,N-Diisopropylethylamine [DIEA]. In some embodiments, the solvent is water. In some embodiments, the solvent is N-methylpyrrolidone (NMP). In some embodiments, the carboxylic acid group activating compound converts the carboxylic acid to a carbonyl group (i.e., carboxylic acid group activation). In some embodiments, the carboxylic acid group is activated for 5, 10, 15, 20, 30, 45, or 60 minutes after exposure to an activation formulation.

In some aspects, the activation formulation comprises 4% by weight of 1-ethyl-3-(3-dimethylaminopropyl) carbodiimide and 2% by weight of N-hydroxysuccinimide (NHS) dissolved in deionized water. In some aspects, the activation formulation comprises 4% by weight of 1,3-Diisopropylcarbodiimide (DIC) and 2% by weight of hydroxybenzotriazole (HOBt) dissolved in NMP. In some aspects, the activation formulation comprises 4% by weight of (O-(7-azabenzotriazol-1-yl)-N,N,N',N'-tetramethyluronium hexafluorophosphate) (HATU) and 2% by weight of N,N-Diisopropylethylamine (DIEA) dissolved in NMP. In some aspects, the activation formulation comprises 4% by weight of Benzotriazol-1-yl-oxytripyrrolidinophosphonium hexafluorophosphate (PyBOP) and 2% by weight of N,N-Diisopropylethylamine (DIEA) dissolved in NMP.

In some embodiments, the carboxylic acid group activating compound is a carbodiimide precursor. In one aspect, the carbodiimide precursor is converted to a carbodiimide through exposure to radiation, e.g., ultraviolet radiation. In an embodiment, the carbodiimide precursor is a thione. The carbodiimide precursor may also be referred to as a photoactivated carbodiimide. In an embodiment, photoactivated carbodiimides are used to provide site-specific activation of carboxylic acid groups on an array by spatially controlling exposure of the photoactivated carbodiimide solution to electromagnetic radiation at a preferred activation wavelength. In some embodiments, the preferred activation wavelength is 248 nm.

In an embodiment, the carbodiimide precursor is a thione that is converted to carbodiimide via photoactivation. In one aspect, the thione is converted to a hydroxymethyl phenyl carbodiimide after exposure to electromagnetic radiation. In some embodiments, the thione is 4,5-dihydro-4-(hydroxymethyl)-1-phenyl-1H-tetrazole-5-thione, 1-ethyl-4-dimethylaminopropyl tetrazole 5-thione, 1,3-Bis(2,2-dimethyl-1,3-dioxolan-4-ylmethyl)-5-thione, 4-cyclohexyl-1H-tetrazole-5(4H)-thione, or 1-phenyl-4-(piperidinomethyl) tetrazole-5(4H)-thione.

In some embodiments, the activation solution comprises a carbodiimide precursor, a solvent, and a polymer. In an embodiment, the carbodiimide precursor is 4,5-dihydro-4-(hydroxymethyl)-1-phenyl-1H-tetrazole-5-thione, 1-ethyl-4-dimethylaminopropyl tetrazole 5-thione, or 1,3-Bis(2,2-dimethyl-1,3-dioxolan-4-ylmethyl)-5-thione. In some aspects, the carbodiimide precursor is present in the activation solution at a concentration of 2.5% by weight. In some aspects the carbodiimide precursor is present in the activation solution at a concentration of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or 5.0% by weight of the total formulation concentration.

In some embodiments, the solvent is water. In some aspects, the solvent is about 80-90% by weight of the total formulation concentration. In some aspects, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some aspects, a polymer is a polyvinyl pyrrolidone and/or a polyvinyl alcohol. In some aspects, a polymer is about 0.5-5% by weight of the total formulation concentration. In some aspects, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some aspects, a coupling reagent is a carbodiimide. In some aspects, a coupling reagent is a triazole. In some aspects, a coupling reagent is 1-ethyl-3-(3-dimethylaminopropyl) carbodiimide. In some aspects, a coupling reagent is about 0.5-5% by weight of the total formulation concentration. In some aspects, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

Linker Formulations

Also disclosed herein is a linker formulation. A linker formulation can include components such as a solvent, a polymer, a linker molecule, and a coupling reagent. In some aspects, the polymer is 1% by weight polyvinyl alcohol and 2.5% by weight poly vinyl pyrrolidone, the linker molecule is 1.25% by weight polyethylene oxide, the coupling reagent is 1% by weight 1-ethyl-3-(3-dimethylaminopropyl) carbodiimide, and the solvent includes water. In some aspects, the polymer is 0.5-5% by weight polyvinyl alcohol and 0.5-5% by weight poly vinyl pyrrolidone, the linker molecule is 0.5-5% by weight polyethylene oxide, the coupling reagent is 0.5-5% by weight 1-ethyl-3-(3-dimethylaminopropyl) carbodiimide, and the solvent includes water.

In some aspects, the solvent is water, an organic solvent, or a combination thereof. In some aspects, the organic solvent is N Methyl pyrrolidone, Di methyl formamide, Di chloromethane, Di methyl sulfoxide, or a combination thereof. In some aspects, the solvent is about 80-90% by weight of the total formulation concentration. In some aspects, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some aspects, a polymer is a polyvinyl pyrrolidone and/or a polyvinyl alcohol. The general structure of polyvinyl alcohol is as follows, where n is any positive integer greater than 1:

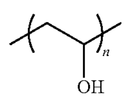

In some aspects, a polymer is about 0.5-5% by weight of the total formulation concentration. In some aspects, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

A linker molecule can be a molecule inserted between a surface disclosed herein and peptide that is being synthesized via a coupling molecule. A linker molecule does not necessarily convey functionality to the resulting peptide, such as molecular recognition functionality, but can instead elongate the distance between the surface and the peptide to enhance the exposure of the peptide's functionality region(s) on the surface. In some aspects, a linker can be about 4 to about 40 atoms long to provide exposure. The linker molecules can be, for example, aryl acetylene, ethylene glycol oligomers containing 2-10 monomer units (PEGs), diamines, diacids, amino acids, and combinations thereof. Examples of diamines include ethylene diamine and diamino propane. Alternatively, linkers can be the same molecule type as that being synthesized (e.g., nascent polymers or various coupling molecules), such as polypeptides and polymers of amino acid derivatives such as for example, amino hexanoic acids. In some aspects, a linker molecule is a molecule having a carboxylic group at a first end of the molecule and a protecting group at a second end of the molecule. In some aspects, the protecting group is a t-Boc protecting group or an Fmoc protecting group. In some aspects, a linker molecule is or includes an aryl acetylene, a polyethyleneglycol, a nascent polypeptide, a diamine, a diacid, a peptide, or combinations thereof. In some aspects, a linker molecule is about 0.5-5% by weight of the total formulation concentration. In some aspects, a linker molecule is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

The unbound portion of a linker molecule, or free end of the linker molecule, can have a reactive functional group which is blocked, protected, or otherwise made unavailable for reaction by a removable protective group, e.g., t-Boc or F-Moc as noted above. The protecting group can be bound to a monomer, a polymer, or a linker molecule to protect a reactive functionality on the monomer, polymer, or linker molecule. Protective groups that can be used include all acid and base labile protecting groups. For example, peptide amine groups can be protected by t-butoxycarbonyl (t-BOC or BOC) or benzyloxycarbonyl (CBZ), both of which are acid labile, or by 9-fluorenylmethoxycarbonyl (FMOC), which is base labile.

Additional protecting groups that can be used include acid labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha,alpha-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9 fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio) carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl. (See also, Greene, T. W., Protective Groups in Organic Synthesis, Wiley-Interscience, NY, (1981)).

Arrays with Electrodes for Applying Voltage to the Surface of the Array

Figure 5:
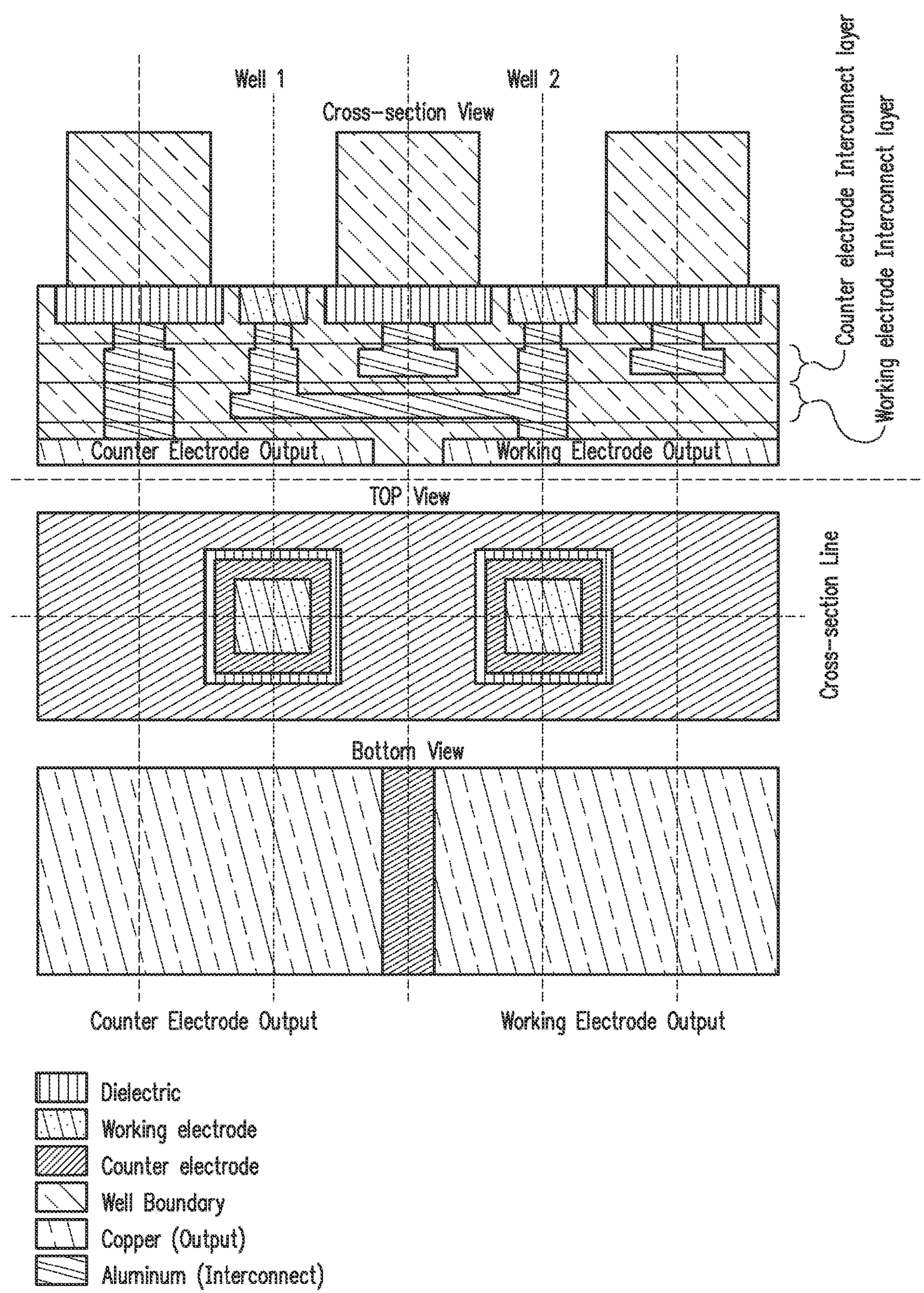
FIG. 5 illustrates a cross-sectional view, top view, and bottom view of the electrode and well configuration of an array. In an embodiment, the array is used with the electrochemiluminescence detection methods described herein.

Also described herein is a system for enhancing electrochemiluminescence on a silicon platform to provide a significant increase in the number of working electrodes/counter electrodes that can be accommodated for a single assay pillar. FIG. 5 shows one embodiment of a configuration of working electrodes and counter electrode across two wells on an array or pillar. In cross-sectional view (FIG. 5 top panel), it is a four layer integrated circuit. The top layer defines location of working electrode and counter electrode, which are isolated by dielectric material. Peptides or other capture ligands (e.g., antigen binding proteins such as antibodies, scFvs or the like) are synthesized in situ or otherwise coupled (e.g., using carbodiimide chemistry) on the surface of a working electrode. The middle two layers are metal interconnection layers to connect and group counter electrode or working electrode, which are also isolated by dielectric material. The bottom layer includes the outputs of working electrode and counter electrode, which are connected to a power supply or control unit. In top view (FIG. 5, middle panel), each array feature has its own working electrode and counter electrode, which are used to generate an electrical potential difference when the electrodes are powered. Bottom view (FIG. 5, bottom panel) shows an example of electrode output. According to design choices for feature grouping, the electrode output layout will differ, as described below.

Figure 6:
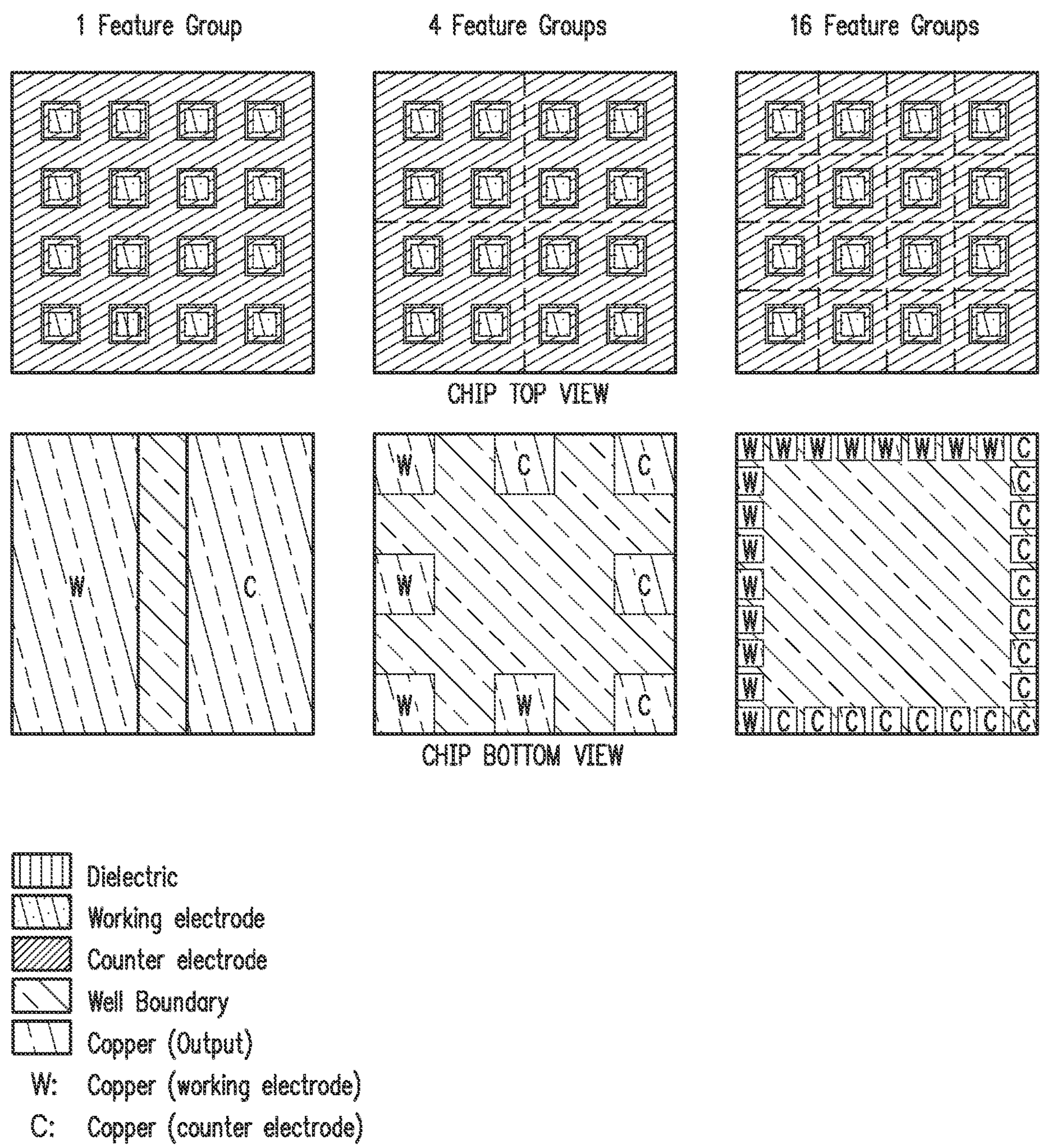
FIG. 6 shows a top and bottom view for chips (including an embodiment of electrode and well configurations) comprising 1 feature group, 4 feature groups, or 16 feature groups.

FIG. 6 shows a view of 16 features on a microarray chip according to 3 different embodiments. In an embodiment, 1 "feature group" is detected, allowing detection and quantitation of up to one biomolecule of interest (top left). In another embodiment 4 "feature groups" are detected, allowing detection and quantitation of up to four biomolecules of interest (top middle). In another embodiment 16 "feature groups" are detected, allowing detection and quantitation of up to 16 biomolecules of interest (top right). Working and counter electrode outputs are shown in the chip bottom view. In some embodiments, the microarray chip comprises 2, 4, 8, 16, 32, 64, 100, 200, 500, 1000, 2000, 5000, 10,000, 15,000, 20,000, 30,000, 40,000, 50,000, 60,000, 70,000, 80,000, 90,000, 1,000,000, 1, 500,000, 2,000,000 or more working electrodes or electrode pairs. In some embodiments, the microarray chip includes multiple electrode pairs wherein each feature associated with these multiple electrode pairs includes the same capture ligand to capture the same analyte. In some embodiments the microarray includes the same number of counter electrodes as working electrode and is configured to detect a single analyte or multiple distinct analytes on a chip. By having the same number of counter and working electrodes, the voltage applied to a feature can be precisely controlled. In some embodiments, 500 or more analytes (e.g., for triplicate measurements, one third the total of number of features, such as described above) that can be detected on one chip. Statistically robust data can be obtained by having multiple features having the same capture ligand.

Microarrays of the present invention can include features as small as 50 nm on edge because the amplified ECL tag system produces extremely high signal to noise ratios. In some embodiments, the features have an edge dimension between 50 nm and 1 um. In other embodiments, the features have an edge dimension between 50 nm and 100 nm. In yet other embodiments, the edge dimension is between 50 nm and 75 nm. We have demonstrated reliable and accurate detection of target biomolecules to AECL microarrays having features as small as 50 nm on edge notwithstanding the reduced number of capture ligands and bound targets as compared to larger features. Assuming constant capture ligand density, the number of capture ligands per feature is a function of feature area. Thus as compared to a square feature having an edge length of 100 nm, a 50 nm feature would have ¼ the number of capture ligands. By using the AECL approach and a 50 nm feature length, a 3 mm×3 mm microarray chip can typically include anywhere from 200, 000 to 2,000,000 features.

Figure 7:
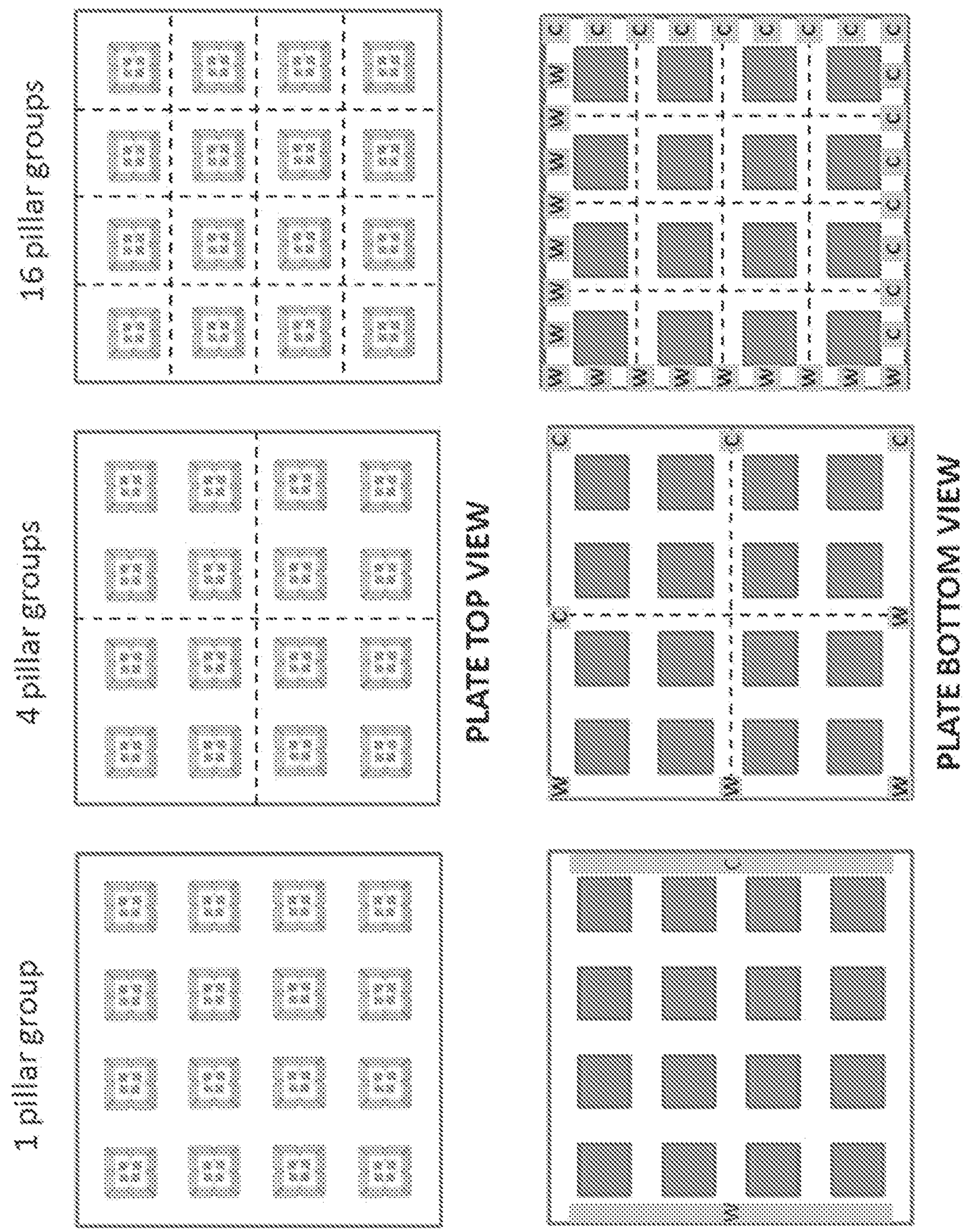
FIG. 7 shows top and bottom view for chips comprising 1 pillar group, 4 pillar groups, or 16 pillar groups.

In FIG. 7, an AECL assay plate array is shown in an embodiment comprising a set of 16 pillars, each of which receives and supplies voltage to four separate AECL microarray chips. Three different pillar groupings are shown, in which the AECL assay plate is divided into 1 pillar group (left panel), 4 pillar groups (middle panel), or 16 pillar groups (right panel). The bottom view shows, according to each embodiment, working and counterelectrode configurations for each number of pillar groups.

Figure 8:
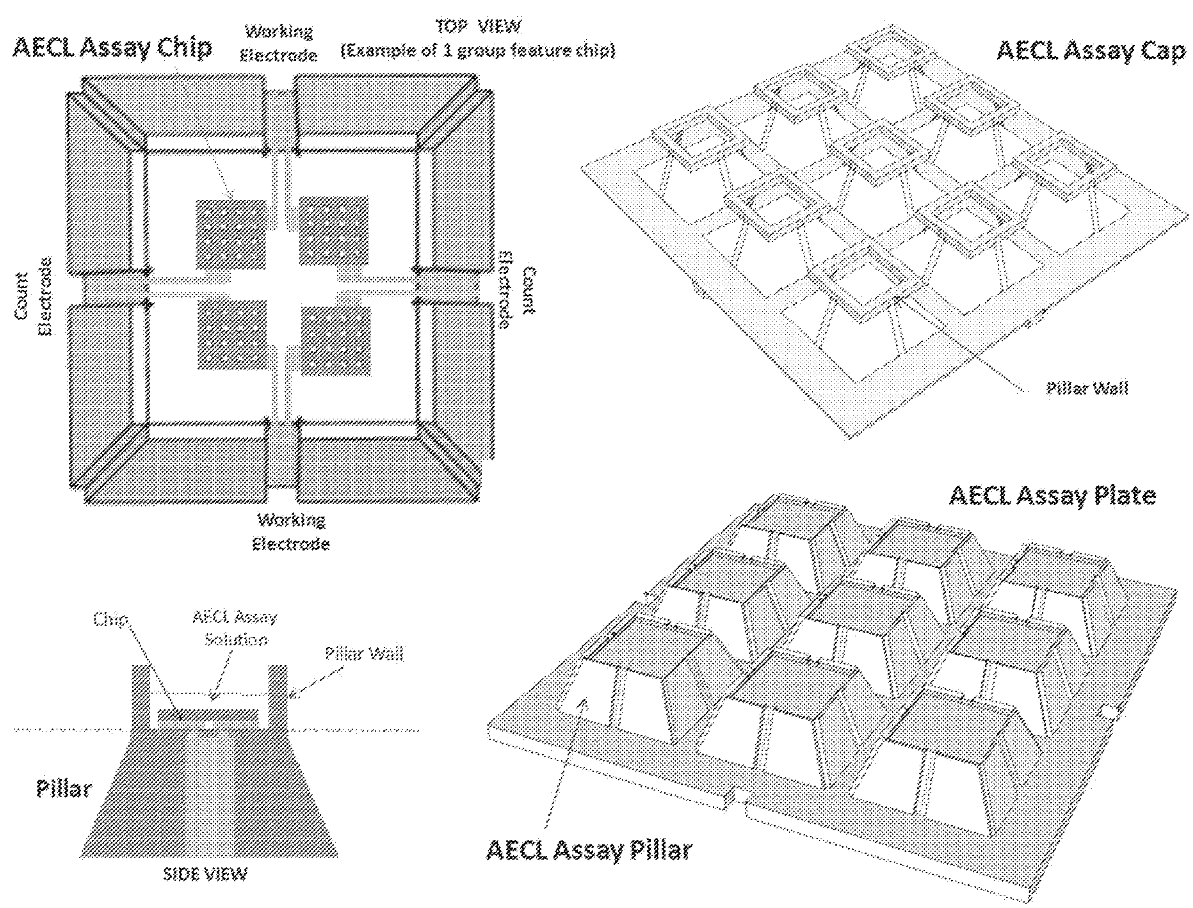
FIG. 8 shows a detailed diagram of an AECL pillar mount (top left) onto which four AECL microarray assay chips are mounted. An AECL assay cap (top right) is used to cover the AECL assay plate (bottom right) which as shown, includes 9 separate pillar mounts. The assay cap includes pillar walls mounted on struts that engage grooves on the sides of the assay plate pillars. In connection with the top surface of the pillar mount, the pillar walls form a reservoir that retains the AECL assay solution (see side view, bottom left).

FIG. 8 shows a detailed view of an AECL assay plate, according to an embodiment of the invention. The counter electrodes ("count electrode" in FIG. 8) and working electrodes are attached to the array at the top of the pillar mount (top left panel). The array can be divided into multiple sections, with a counter electrode and working electrode attached to each. An AECL assay cap (top right panel) mounts onto an exemplary AECL assay plate (bottom right panel), that includes nine AECL pillar mounts (i.e., the structure shown in the top left panel), each of which, in this example, receives and supplies voltage to four separate AECL microarray chips. The assay cap includes pillar walls that contain the assay solution when the cap is mounted onto the assay plate. See FIG. 8 bottom left (side view) and top right (assay cap). Bottom left panel (side view) shows AECL microarray ("chip") mounted on pillar and covered with AECL assay solution. The number of assay pillars included in an assay plate can be selected according to the number of different assays sought to be carried out. For example, the assay plate can include 24, 96, 384 or 1586 pillars in conformity with standard microtiter plate configurations.

Figure 9:
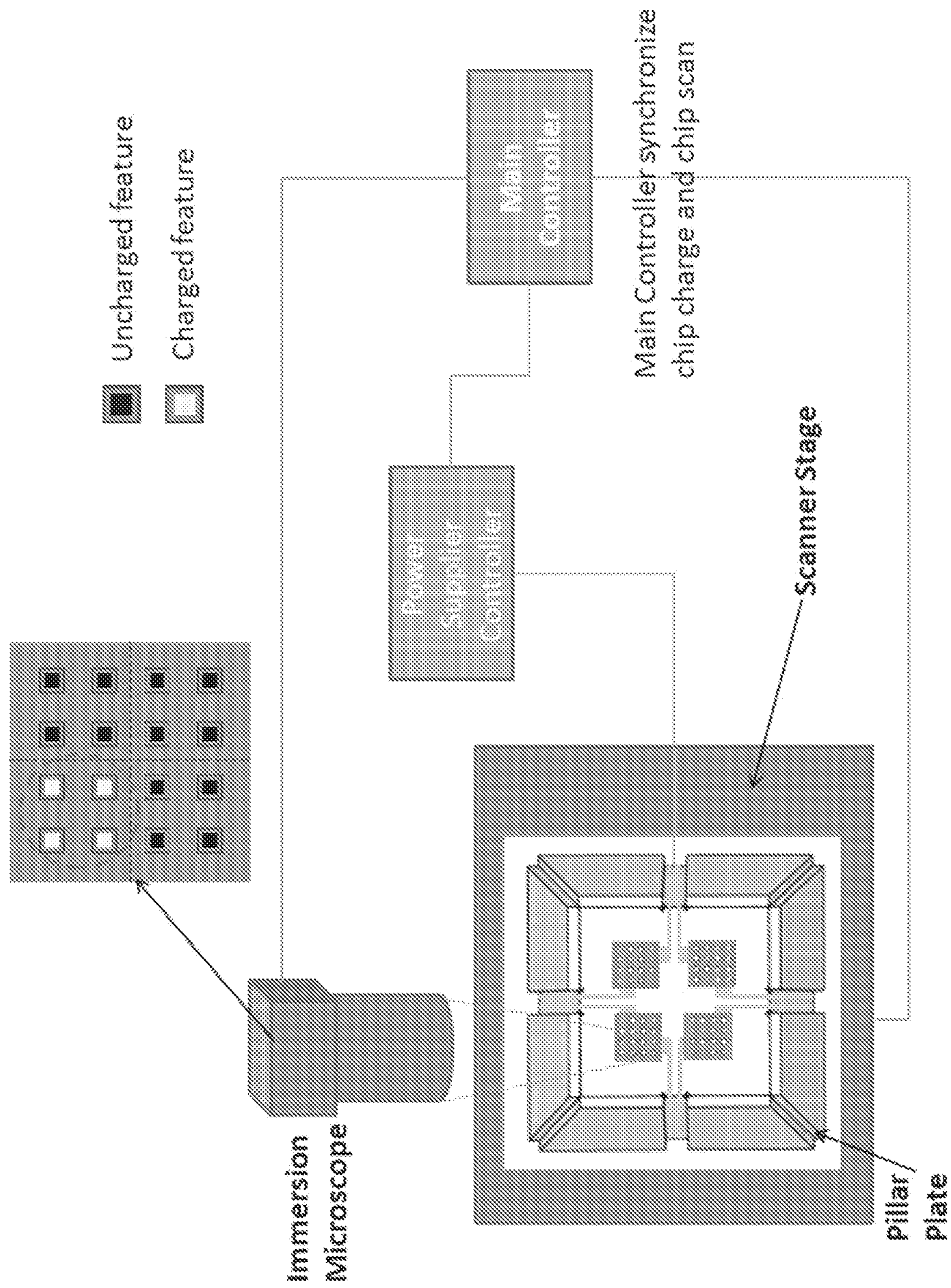
FIG. 9 shows a diagram of AECL detection of analytes on a single pillar on an assay plate.

FIG. 9 diagrams an exemplary system for detecting biomolecules bound to an AECL microarray chip, according to an embodiment of the invention. Voltage is applied to selected working and counter electrode leads array via a main controller attached to a power supplier controller. After applying voltage to the array, AECL tags illuminate features comprising bound target biomolecules of interest, as described in this specification. The luminescence is. The chip is placed on a scanner stage and luminescence is optically detected.

In an embodiment, the system optics employ a wet (i.e., immersion) microscope lens stepping and scanning at a very minimal distance from the pillar top (approx. 0.5 mm) to increase the numerical aperture and reduces the loss of light from AECL. The control of the system can be completely automated such that individual electrodes can be turned on and off, at times precisely coinciding with optimal placement of array features with respect to the optics for image capture thus minimizing loss of signal from signal decay of light.

Methods of Manufacturing Arrays

Methods of Attaching Biomolecules to an Array

Also disclosed herein are methods for manufacturing arrays. In some aspects, capture ligands positioned at predetermined locations on microarrays disclosed herein can be synthesized in situ on a surface, e.g., a substrate disclosed herein. In some instances, the arrays are made using photolithography. For example, the substrate is contacted with a photoactive coupling solution. Masks can be used to control radiation or light exposure to specific locations on a surface provided with free linker molecules or free coupling molecules having protecting groups. In the exposed locations, the protecting groups are removed, resulting in one or more newly exposed reactive moieties on the coupling molecule or linker molecule. The desired linker or coupling molecule is then coupled to the unprotected attached molecules, e.g., at the carboxylic acid group. The process can be repeated to synthesize a large number of features in specific or positionally-defined locations on a surface (see, for example, U.S. Pat. No. 5,143,854 to Pirrung et al., U.S. Patent Application Publication Nos. 2007/0154946 (filed on Dec. 29, 2005), 2007/0122841 (filed on Nov. 30, 2005), 2007/0122842 (filed on Mar. 30, 2006), 2008/0108149 (filed on Oct. 23, 2006), and 2010/0093554 (filed on Jun. 2, 2008), each of which is herein incorporated by reference).

In some aspects, a method of producing a three-dimensional (e.g., porous) array of features, can include obtaining a porous layer attached to a surface; and attaching the features to the porous layer, said features each comprising a collection of peptide chains of determinable sequence and intended length, wherein within an individual feature, the fraction of peptide chains within said collection having the intended length is characterized by an average coupling efficiency for each coupling step of at least about 98%. In some aspects, the features are attached to the surface using a photoactive coupling formulation, comprising a photoactive compound, a coupling molecule, a coupling reagent, a polymer, and a solvent. In some aspects, the features are attached to the surface using a photoactive coupling formulation disclosed herein. In some aspects, the photoactive coupling formulation is stripped away using water.

In an embodiment, described herein is a process of manufacturing an array. A surface comprising attached carboxylic acid groups is provided. The surface is contacted with a photoactive coupling solution comprising a photoactive compound, a coupling molecule, a coupling reagent, a polymer, and a solvent. The surface is exposed to ultraviolet light in a deep ultra violet scanner tool according to a pattern defined by a photomask, wherein the locations exposed to ultraviolet light undergo photo base generation due to the presence of a photobase generator in the photoactive coupling solution. The expose energy can be from 1 mJ/cm$^2$ to 100 mJ/cm$^2$ in order to produce enough photobase.

The surface is post baked upon exposure in a post exposure bake module. Post exposure bake acts as a chemical amplification step. The baking step amplifies the initially generated photobase and also enhances the rate of diffusion to the substrate. The post bake temperature can vary between 75° C. to 115° C., depending on the thickness of the porous surface, for at least 60 seconds and not usually exceeding 120 seconds. The free carboxylic acid group is coupled to the deprotected amine group of a free peptide or polypeptide, resulting in coupling of the free peptide or polypeptide to the carboxylic acid group attached to the surface. This surface can be a porous surface. The synthesis of peptides coupled to a carboxylic acid group attached to the surface occurs in an N→C synthesis orientation, with the amine group of free peptides attaching to carboxylic acid groups bound to the surface of the substrate. Alternatively, a diamine linker may be attached to a free carboxylic acid group to orient synthesis in a C→N direction, with the carboxylic acid group of free peptides attaching to amine groups bound to the surface of the substrate.

The photoactive coupling solution can now be stripped away. In some aspects, provided herein is a method of stripping the photoresist completely with DI water. This process is accomplished in a developer module. The wafer is spun on a vacuum chuck for, e.g., 60 seconds to 90 seconds and deionized water is dispensed through a nozzle for about 30 seconds.

The photoactive coupling formulation may be applied to the surface in a coupling spin module. A coupling spin module can typically have 20 nozzles or more to feed the photoactive coupling formulation. These nozzles can be made to dispense the photoactive coupling formulation by means of pressurizing the cylinders that hold these solutions or by a pump that dispenses the required amount. In some aspects, the pump is employed to dispense 5-8 cc of the photoactive coupling formulation onto the substrate. The substrate is spun on a vacuum chuck for 15-30 seconds and the photoactive coupling formulation is dispensed. The spin speed can be set to 2000 to 2500 rpm.

Optionally, a cap film solution coat is applied on the surface to prevent the unreacted amino groups on the substrate from reacting with the next coupling molecule. The cap film coat solution can be prepared as follows: a solvent, a polymer, and a coupling molecule. The solvent that can be used can be an organic solvent like N methyl pyrrolidone, di methyl formamide, or combinations thereof. The capping molecule is typically acetic anhydride and the polymer can be Poly vinyl pyrrolidone, polyvinyl alcohol, polymethyl methacrylate, poly (methyl iso propenyl) ketone, or poly (2 methyl pentene 1 sulfone). In some embodiments, the capping molecule is ethanolamine This process is done in a capping spin module. A capping spin module can include one nozzle that can be made to dispense the cap film coat solution onto the substrate. This solution can be dispensed through pressurizing the cylinder that stores the cap film coat solution or through a pump that precisely dispenses the required amount. In some aspects, a pump is used to dispense around 5-8 cc of the cap coat solution onto the substrate. The substrate is spun on a vacuum chuck for 15-30 s and the coupling formulation is dispensed. The spin speed can be set to 2000 to 2500 rpm.

The substrates with the capping solution are baked in a cap bake module. A capping bake module is a hot plate set up specifically to receive wafers just after the capping film coat is applied. In some aspects, provided herein is a method of baking the spin coated capping coat solution in a hot plate to accelerate the capping reaction significantly. Hot plate baking generally reduces the capping time for amino acids to less than two minutes.

The byproducts of the capping reaction are stripped in a stripper module. A stripper module can include several nozzles, typically up to 10, set up to dispense organic solvents such as acetone, iso propyl alcohol, N methyl pyrrolidone, Di methyl formamide, DI water, etc. In some aspects, the nozzles can be designated for acetone followed by iso propyl alcohol to be dispensed onto the spinning wafer. The spin speed is set to be 2000 to 2500 rpm for around 20 s.

This entire cycle can be repeated as desired with different coupling molecules each time to obtain a desired sequence.

In some aspects, an array comprising a surface of free carboxylic acids is used to synthesize polypeptides in an N→C orientation. In an embodiment, the carboxylic acids on the surface of the substrate are activated (e.g., converted to a carbonyl) to allow them to bind to free amine groups on an amino acid. In an embodiment, activation of carboxylic acids on the group of the surface can be done by addition of a solution comprising a carbodiimide or succinimide to the surface of the array. In some embodiments, carboxylic acids can be activated by addition of a solution comprising 1-Ethyl-3-(3-dimethylaminopropyl)carbodiimide [EDC], N-hydroxysuccinimide [NHS], 1,3-Diisopropylcarbodiimide [DIC], hydroxybenzotriazole (HOBt), (O-(7-azabenzotriazol-1-yl)-N,N,N',N'-tetramethyluronium hexafluorophosphate) [HATU], benzotriazol-1-yl-oxytripyrrolidinophosphonium hexafluorophosphate [PyBOP], or N,N-Diisopropylethylamine [DIEA] to the surface of the array. The activation solution is washed away and the surface of the array is prepared for addition of an amino acid layer (i.e., one amino acid at each activated carboxylic acid group). Carboxylic acid groups remain activated for up to 2, 3, 4, 5, 6, 7, 8, 9, or 10 hours.

Addition of a solution comprising an amino acid with a free amine group to the activated carboxylic acid surface of the array results in binding of a single amino acid to each carboxylic acid group. In some embodiments, the amino acid comprises an amino acid with protected amine groups. Using a photosensitive chemical reaction, the protecting group can be removed from the amine group of selected amino acids at site-specific locations using a reticle. For example, Fmoc-protected amino acids are mixed in a solution comprising a photobase. Upon exposure of the solution on the array to a specific frequency of light at site-specific locations, the photobase will release a base which will deprotect the amino acid, resulting in coupling of the amino acid to the activated carboxylic acid group on the surface of the array. Another method of generating a base is through the use of a photoacid generator. In some embodiments, the photoacid generator is N-Boc-piperidine or 1-Boc-4-piperazine.

After a completed layer of amino acids is coupled, remaining uncoupled activated carboxylic acids are capped to prevent nonspecific binding of amino acids on subsequent synthesis steps. The steps of activation, addition of an amino acid layer, and capping are repeated as necessary to synthesize the desired polypeptides at specific locations on the array.

In an embodiment, peptides synthesized in the N→C terminus direction can be capped with a diamine molecule to enhance binding properties of selected polypeptide sequences to a biological molecule, e.g., an antibody. In other aspects, peptides synthesized in the C→N direction can be capped with a dicarboxylic acid molecule to enhance binding properties of selected sequences to a biological molecule.

While synthesizing polypeptides in parallel on the surface of an array, the method described herein ensures complete activation of carboxylic acid on the surface of the array. Due to stability of the activated ester for an extended period of time, 2, 3, 4, 5, 6, 7, 8, 9, 10, 11, 12, 13, 14, 15, 16, 17, 18, 19, 20, 21, 22, 23, 24, 25 or more coupling cycles may be completed after a single activation step (e.g., to couple an entire layer of 2-25 or more different amino acids at different locations on the array). As the coupling occurs during hard bake and due to the presence of excess amino acid in the solution, complete 100% deprotection of Fmoc-protected amino acid may not be required for significantly high coupling yields. After addition of all amino acids and capping, all free activated carboxylic acids are either coupled or capped, thus resulting in high efficiency and accuracy of polypeptide synthesis.

In an embodiment, proteins, polypeptides, or other molecules are attached to the activated carboxylic acid group on the surface of the array. After activation of carboxylic acid groups on the array, a solution comprising proteins, polypeptides, or other molecules with a free amine group are added to the surface of the array. The amine group binds to the activated carboxylic acid group, thus attaching the protein, polypeptide, or other molecule to the array. In an embodiment, this method is used to attach antibodies to the surface of the array. In on embodiment, the amine groups are protected, and subsequently deprotected on the surface of the chip. In an embodiment, the deprotection occurs at specified locations on the chip using light shined through a reticle to interact with a photolabile compound, e.g., a photobase or photoacid, which deprotects the protected amine group.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: AECL Wafer Processing

Steps 1-7 are described with reference to FIG. 10A; steps 8-14 are described with reference to FIG. 10B.

Step 1: Silicon wafers were obtained from University wafers. 1000 A silicon dioxide was deposited using thermal oxide deposition in an oxidation chamber.

Step 2: P5107 (photoresist) obtained from Rohm and Haas were coated on the wafers using a RF3S Sokudo coater. Using a working electrode photo mask, these wafers were exposed in a Nikon 5205 DUV at 18 mj/cm2. The wafers were developed in a developer for 60 s. Oxide etch was performed using Hydrofluoric acid (HF) bath for 30 s to remove 1000 A oxide. Photoresist was stripped using Acetone wash followed by Isopropanol wash for 30 s each in a coater. All solvents and HF were obtained from Sigma Aldrich.

Step 3: Uniform thickness of 1500 A Gold was deposited on top of this wafer substrate by sputtering.

Step 4: The wafers were polished in a chemical mechanical planarization (CMP) polisher until oxide layer was reached.

Step 5: P5107 photoresist obtained from Rohm and Haas were coated on the wafers using a RF3S Sokudo coater. Using a counter electrode photo mask, these wafers were exposed in a Nikon 5205 DUV at 18 mj/cm2. The wafers were developed in a developer for 60 s. Oxide etch was performed using Hydrofluoric acid (HF) bath to remove 1000 A oxide. Photoresist was stripped using Acetone wash followed by Isopropanol wash for 30 s each in a coater.

Step 6: Uniform thickness of 1500 A copper was deposited on top of this wafer substrate by sputtering.

Step 7: The wafers were polished in a CMP polisher until oxide layer was reached.

Step 8: Thermal oxide of 1000 A was grown on top of the wafers in an oxidation chamber. P5107 photoresist obtained from Rohm and Haas were coated on the wafers using a RF3S Sokudo coater. Using a interconnect photo mask, these wafers were exposed in a Nikon S205 DUV at 18 mj/cm2. The wafers were developed in a developer for 60 s. Oxide etch was performed using Hydrofluoric acid (HF) bath to remove 1000 A oxide. Photoresist was stripped using Acetone wash followed by Isopropanol wash.

Step 9: Uniform thickness of 500 A Aluminum interconnect was deposited on top of this wafer substrate by sputtering.

Step 10: The wafers were polished in a CMP polisher until the electrodes layer was reached.

Step 11: P5107 photoresist obtained from Rohm and Haas was coated on the wafers using a RF3S Sokudo coater. Using an output photo mask, these wafers were exposed in a Nikon 5205 DUV at 18 mj/cm2. The wafers were developed in a developer for 60 s. Oxide etch was performed using Hydrofluoric acid (HF) bath to remove 1000 A oxide. Photoresist was stripped using Acetone wash followed by Isopropanol wash.

Step 12: Uniform thickness of 500 A copper was deposited on top of this wafer substrate by sputtering.

Step 13: The wafers were polished in a CMP polisher until oxide layer was reached.

Step 14: The wafer was then flipped and photoresist was coated on the wafer backside. Using a photo mask, these wafers were exposed in a Nikon 5205 DUV at 18 mj/cm2. The wafers were developed in a developer for 60 s. Silicon etch was performed using Hydrofluoric acid (HF) bath to remove silicon until the contacts were reached. Photoresist was stripped using Acetone wash followed by Isopropanol wash.

Example 2: Functionalization of Wafer and Dicing into Chips Production

Figure 10:
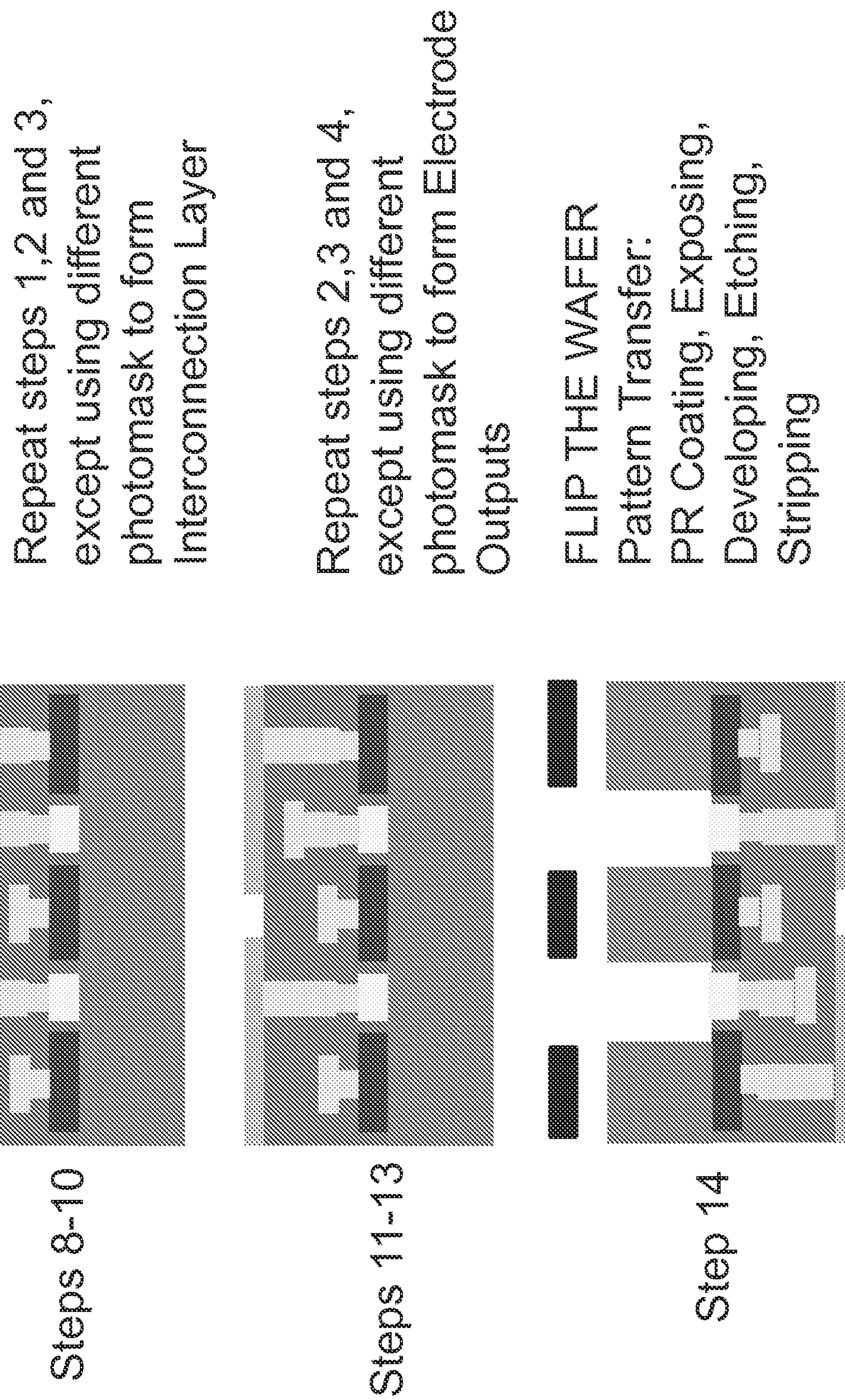
FIGS. 10A and 10B show steps in the AECL chip manufacturing process.

Wafers comprising electrodes as shown in FIGS. 10A and B for supplying voltage to array features were provided according to Example 1. A COOH-functionalized surface was formed as follows on an AECL wafer:

11-Mercaptoundecanoic acid and Acetic Acid were obtained from Sigma Aldrich. Ethanol, Hydrogen Peroxide, Sulfuric Acid are obtained from VWR.

To functionalize with COOH groups, the AECL wafers of Example 1, having gold working electrodes, were cleaned with piranha solution which comprises 50 weight % of pure Sulfuric acid and 50 weight % of Hydrogen Peroxide for 60 minutes. The wafers were then rinsed with DI Water continuously for 5 minutes followed by rinsing with Ethanol for 5 minutes. The wafers were washed with a mixture of 50% Ethanol and 50% DI Water for 10 minutes. The wafers were then contacted with a solution containing 2.5 weight % of 11-Mercaptoundecanoic acid and 97.5 weight % of Pure Ethanol for 12 hours under mild shaking conditions. After 10-12 hours, wafers were then rinsed for Ethanol and isopropanol (IPA) for 5 minutes each. This was followed by washing the wafers with DI Water for 10 minutes and hot acetic acid solution which was prepared by mixing 10 weight % of Acetic acid in 90 weight % of DI Water at 60 C for 45 minutes. Finally, the wafers was rinsed with DI Water and IPA for 5 minutes each and blown dry under nitrogen. Following this step, the wafers were diced into chips of 3.0 mm×3.0 mm.

Example 3: Chip Activation and Anti-TNF-Alpha Antibody Coupling

1-Ethyl-3-(3-dimethylaminopropyl)carbodiimide [EDC], N-hydroxysuccinimide [NHS], Ethanolamine and Phosphate Buffer Saline (PBS) buffer were obtained from Sigma Aldrich. Primary and secondary anti TNF-alpha antibodies and TNF-alpha were obtained from ABCAM. An activation solution of EDC and NHS was prepared by dissolving 4% by weight of EDC and 2% by weight of NHS in deionized water. The activation solution was then applied to the surface of the wafer at room temperature for 10 minutes. The chips were then washed with deionized water for 3 minutes.

The primary anti-TNF alpha antibody was coupled to the chip by adding a solution of 10 ug/ml of antibody in PBS buffer to the surface of the wafer with activated COOH groups for 30 mins, resulting in binding of the COOH groups to free amine of the primary antibody. This was followed by capping of unreacted carboxylic acid groups on the surface with 5 weight % Ethanolamine in 95 weight % DI water for 10 minutes followed by washing the wafer in DI water for 10 minutes.

Example 4: Prototype Pillar Mount for AECL Biochip

FIG. 11A shows steps for preparing a pillar mount for an AECL biochip.

Step 1: Silicon wafers were obtained from University wafers. 1000 A silicon dioxide was deposited using thermal oxide deposition in an oxidation chamber.

Step 2: P5107 (photoresist) obtained from Rohm and Haas were coated on the wafers using a RF3S Sokudo coater. Using an AECL pillar working electrode photo mask, these wafers were exposed in a Nikon 5205 DUV at 18 mj/cm2. The wafers were developed in a developer for 60 s. Oxide etch was performed using Hydrofluoric acid (HF) bath for 30 s to remove 1000 A oxide. Photoresist was stripped using Acetone wash followed by Isopropanol wash for 30 s each in a coater. All solvents and HF were obtained from Sigma Aldrich.

Step 3: Uniform thickness of 1500 A Gold was deposited on top of this wafer substrate by sputtering. The wafers were polished in a chemical mechanical planarization (CMP) polisher until oxide layer was reached.

Step 4: P5107 photoresist obtained from Rohm and Haas were coated on the wafers using a RF3S Sokudo coater. Using an AECL pillar counter electrode photo mask, these wafers were exposed in a Nikon 5205 DUV at 18 mj/cm2. The wafers were developed in a developer for 60 s. Oxide etch was performed using Hydrofluoric acid (HF) bath to remove 1000 A oxide. Photoresist was stripped using Acetone wash followed by Isopropanol wash for 30 s each in a coater.

Step 5: Uniform thickness of 1500 A copper was deposited on top of this wafer substrate by sputtering. The wafers were polished in a CMP polisher until oxide layer was reached.

Figure 11:
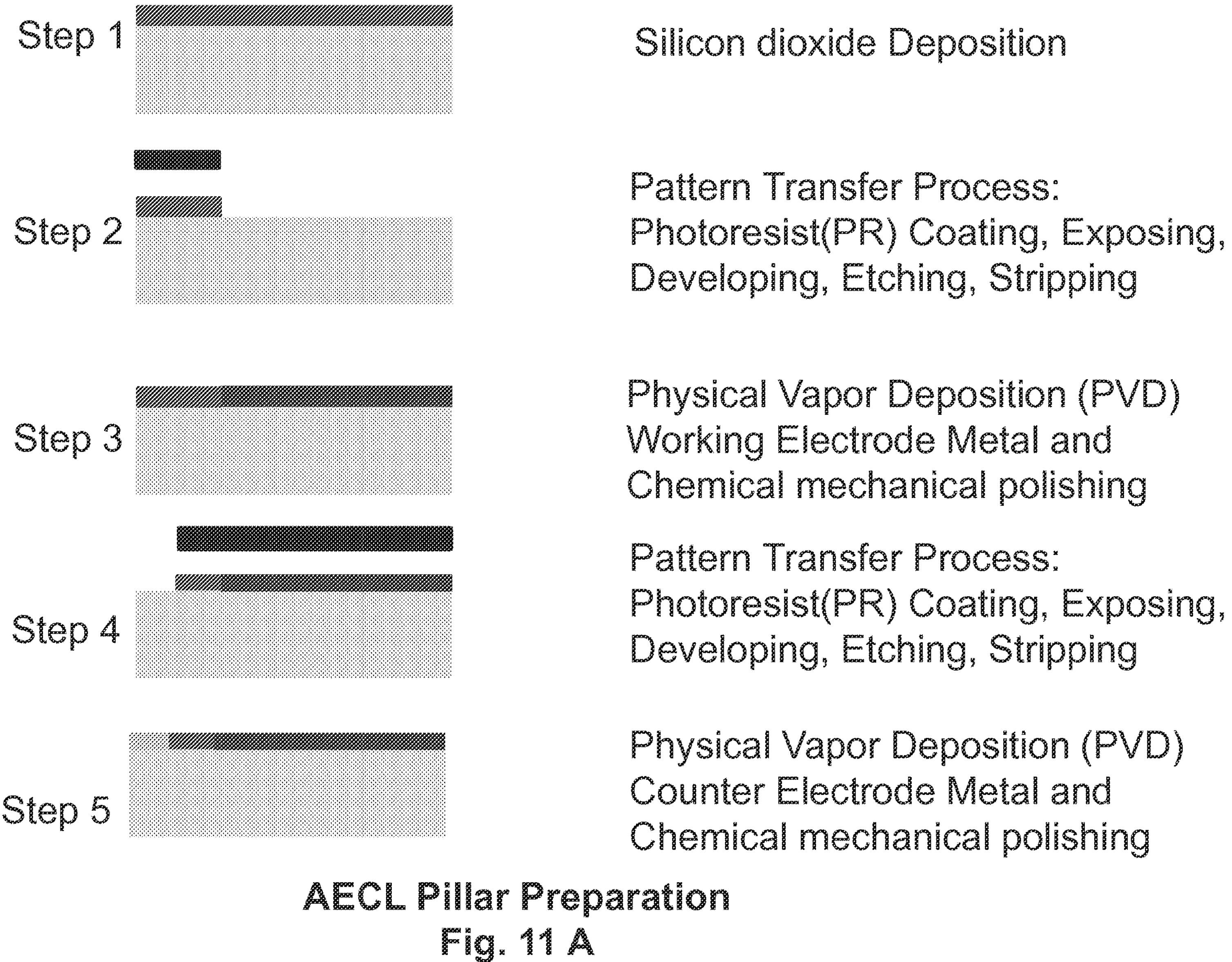
FIGS. 11A and 11B respectively show steps in the AECL pillar mount manufacturing process and a top view of an AECL pillar mount according to an embodiment of the invention.
Figure 11:
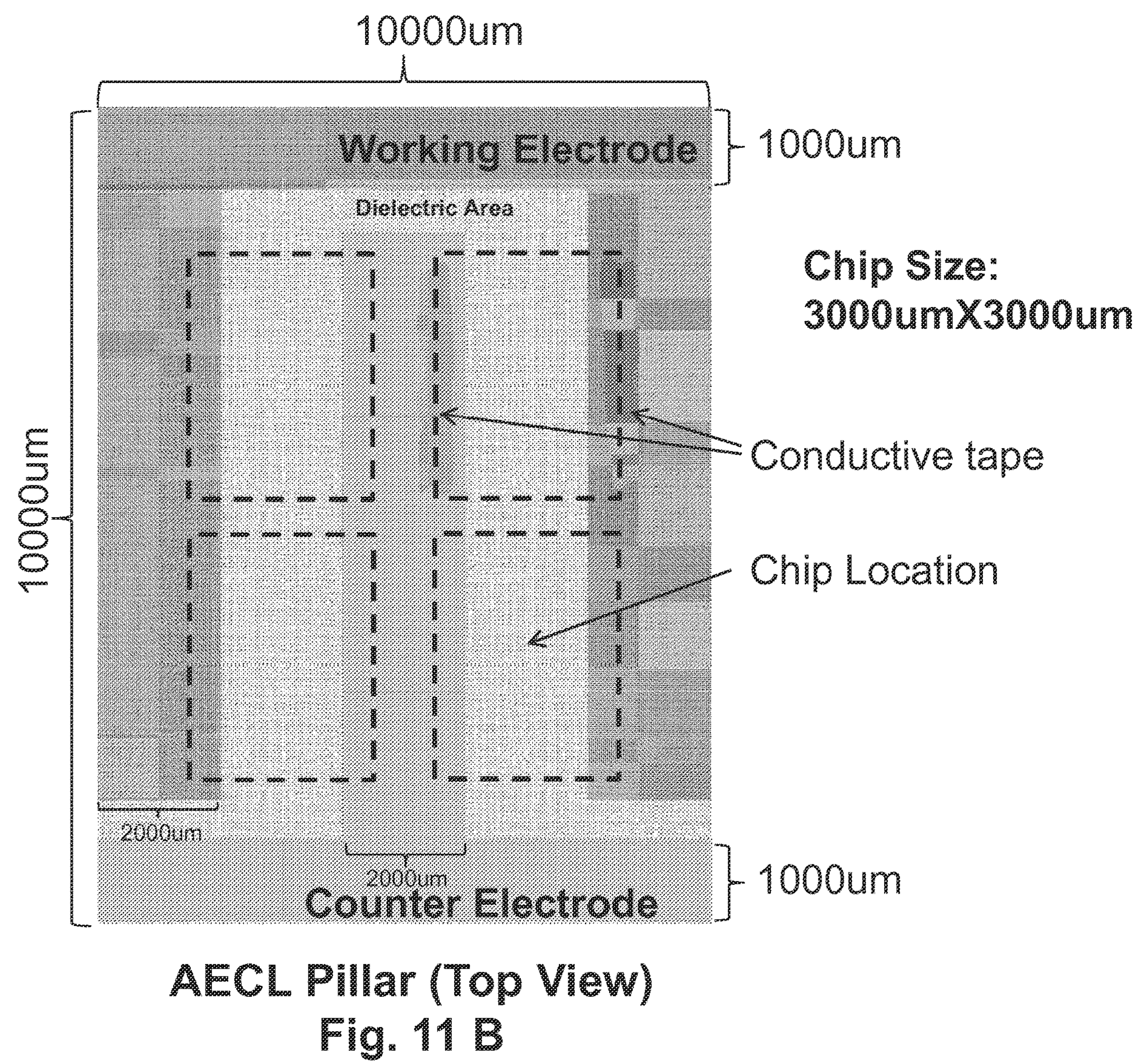

FIG. 11 B shows a top view of a pillar mount used for an AECL biochip, prepared according to the steps outlined above in this example. To test the performance of the AECL-TNF alpha chips, an AECL biochip was mounted on the pillar as follows:

The AECL biochip's working and counter electrodes were picked and placed over the AECL pillar mount. Positional correspondence and electrical contact between the pillar mount and chip working and counter electrodes were stabilized using conductive tape obtained from 3M. The AECL pillar mount working and counter electrodes were connected via copper clips to a model XP-100 voltage controller from Elenco which supplies from 1.5 to 12V.

Example 5: Preparation of an AECL Tag

This example describes preparation of an amplified electrochemiluminescent tag. In this example, ruthenium bis(2,2 bipyridine) bis (2,2 dicarboxylic acid ester) is the electrochemiluminescent moiety, and tyramide is the signal amplification moiety (FIG. 1) through which a plurality of AECL tags bind to target molecules in the vicinity of peroxidase activity (e.g., HRP enzyme) and an oxidizing agent (e.g., hydrogen peroxide).

50 ul of 0.01M of tyramine.HCL and 50 ul of 0.01M of Ruthenium bis(2,2 bipyridine) bis (2,2 dicarboxylic acid) ester were mixed in DI water with the presence of 5 ul of N,N-Diisopropylethylamine (DIEA). The mixture was shaken on a rotary mixer set at 400 rpm for 2 hours, followed by addition of 1 ul of ethanolamine and then shaken again for an additional 10 minutes. TLC was used to purify the solution and the resulting solution was desalted and lyophilized to obtain 0.56 mg of the AECL tag shown in FIG. 1. The AECL tag was dissolved in volume of PBS buffer to generate a 0.5 mg/mL stock solution.

Example 6: TNF-Alpha AECL Assay

Figure 12:
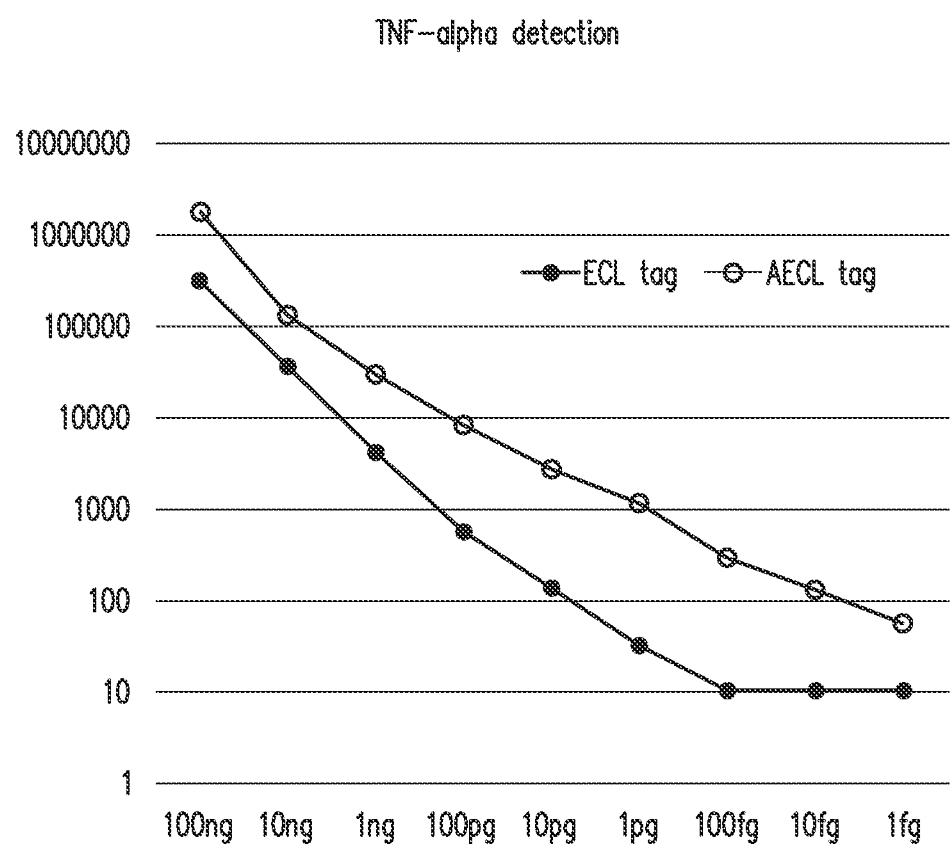
FIG. 12 compares results of ECL and AECL biochip assays for TNF-alpha according to an embodiment of the invention. Y-axis is luminescence in arbitrary units, X-axis is amount of TNF-alpha/mL in assayed sample solution. Thus 100 ng on X-axis corresponds to a TNF-alpha concentration of 100 ng/mL in the assayed sample solution.

TNF alpha was dissolved in varying concentration of 1 fg/mL to 100 ng/mL in PBST (PBST contains 3.2 mM Na2HPO4, 0.5 mM KH2PO4, 1.3 mM KCl, 135 mM NaCl, 0.05% Tween® 20, pH 7.4) and was added to the AECL chips on the pillar substrate. This was incubated for 30 mins at 37 c. After this, the chips were washed with PBST buffer for 5 mins. A secondary TNF-alpha Ab-HRP conjugate obtained from ABcam, was added in a dilution of 1:1000 in PBST and incubated for 15 mins at 37 c. Then a tag solution was made that included a 1:10 dilution in PBS of the AECL tag stock solution and 0.003 weight % hydrogen peroxide. This was added to the chips resulting in binding of multiple AECL tags to the captured TNF alpha/antibody-HRP complexes. Tripropylamine (TPA) was added to the chip in a concentration of 0.1M in an 0.02% sodium acetate buffer with Tween 20. The electrical potential at working electrode was ramped from 0 to 3.5V. The intensity of AECL was read by a CCD camera at 620 nm. A similar assay was also conducted that differed by using an ECL tag obtained from Meso Scale Diagnostics. The data from both assays are shown in FIG. 12. The AECL tag can clearly detect TNF alpha in sub-picogram/mL ranges whereas an ECL tag can only detect pictogram/mL level ranges.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method of detecting a target biomolecule, comprising
   contacting a sample comprising said target biomolecule with a capture ligand, said capture ligand being immobilized at a defined location on a substrate and capable of specifically binding said target biomolecule thereby immobilizing said target biomolecule at said defined location on said substrate;
   contacting said immobilized target biomolecule with a detection ligand, said detection ligand comprising an antibody or antigen-binding fragment capable of specifically binding to said immobilized target biomolecule and wherein said antibody or antigen binding fragment is conjugated to a peroxidase enzyme, thereby forming an immobilized target biomolecule-detection ligand complex;
   contacting said complex with a tagging solution comprising a plurality of AECL tags under conditions that promote covalent binding of said plurality of AECL tags to said complex, wherein each of the AECL tags comprises a ruthenium metal chelate and a tyramide bound to said ruthenium metal chelate, and wherein said tagging solution further comprises hydrogen peroxide;
   washing said substrate to remove unbound AECL tags from said substrate;
   contacting said substrate with a detection solution that reacts with said bound AECL tags to generate luminescence when a voltage is applied to said defined location on said substrate, wherein said detection solution comprises tripropylamine;
   applying said voltage to said defined location on said substrate; and
   measuring the luminescence from said defined location on said substrate thereby detecting said target biomolecule.

2. The method of claim 1, wherein said defined location on said substrate comprises a microarray feature or a plurality of microarray features.

3. The method of claim 2, wherein said feature or features have a width between 50 nm and 1 um.

4. The method of claim 3, wherein said width is between 50 nm and 100 nm.

5. The method of claim 4, wherein said width is between 50 nm and 75 nm.

6. The method of claim 1, wherein said capture ligand is covalently bound to said defined location on said substrate via a COOH moiety provided on said substrate.

7. The method of claim 1, wherein said capture ligand is covalently bound to said defined location on said substrate via an NH2 moiety provided on said substrate.

8. The method of claim 1, wherein said capture ligand and said detection ligand comprise antibodies.

9. The method of claim 1, wherein said capture ligand comprises a peptide.

10. The method of claim 1, wherein said capture ligand comprises a protein.

11. The method of claim 1, wherein said target biomolecule comprises a peptide.

12. The method of claim 1, wherein said target biomolecule comprises a protein.

13. The method of claim 12, wherein said protein is an antibody.

14. The method of claim 1, wherein said sample comprises, blood, serum, plasma, saliva, urine, feces or cerebrospinal fluid (CSF).

15. The method of claim 1, wherein said sample is obtained from a human.

16. The method of claim 1, wherein said detection ligand comprises an antibody-horseradish peroxidase conjugate.

17. The method of claim 1, wherein at least 2, 5, 10, 20, 50, 100, 200, 500, or 1,000 AECL tags are bound to said complex.

18. The method of claim 1, wherein said AECL tag comprises tris (bipyridine) ruthenium(II).

19. The method of claim 1, wherein said AECL tag comprises,

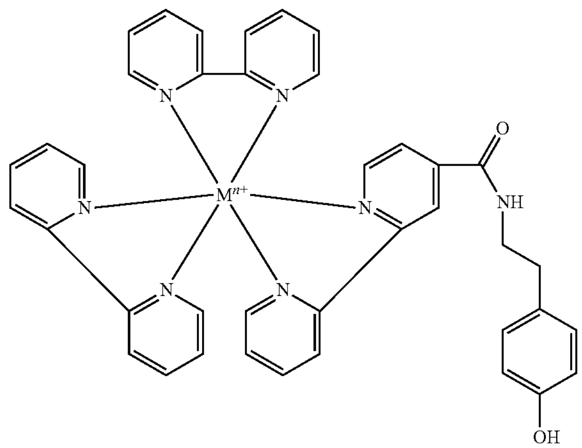

wherein $M^{n+}$ is $Ru^{2+}$.

20. The method of claim 1, wherein the method detects said target biomolecule in the sample at 1 fg/mL concentrations.

* * * * *